United States Patent
Robertson

(10) Patent No.: US 9,370,412 B2
(45) Date of Patent: Jun. 21, 2016

(54) BODILY IMPLANTS AND METHODS FOR DELIVERY AND PLACEMENT OF BODILY IMPLANTS INTO A PATIENTS BODY

(71) Applicant: David W. Robertson, Framingham, MA (US)

(72) Inventor: David W. Robertson, Framingham, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 302 days.

(21) Appl. No.: 13/708,217

(22) Filed: Dec. 7, 2012

(65) Prior Publication Data

US 2013/0150662 A1    Jun. 13, 2013

Related U.S. Application Data

(60) Provisional application No. 61/568,967, filed on Dec. 9, 2011.

(51) Int. Cl.
*A61F 2/00* (2006.01)
*A61B 17/00* (2006.01)
*A61B 17/06* (2006.01)

(52) U.S. Cl.
CPC ............ *A61F 2/0063* (2013.01); *A61F 2/0045* (2013.01); *A61B 17/06109* (2013.01); *A61B 2017/00805* (2013.01); *A61B 2017/00818* (2013.01); *A61B 2017/06104* (2013.01); *A61F 2220/0016* (2013.01)

(58) Field of Classification Search
CPC ............... A61F 2/0063; A61F 2/0045; A61F 2220/0016; A61B 2017/00818; A61B 2017/06104; A61B 17/06109; A61B 2017/00805
See application file for complete search history.

(56) References Cited

U.S. PATENT DOCUMENTS

| | | | |
|---|---|---|---|
| 6,911,003 B2 * | 6/2005 | Anderson et al. | 600/30 |
| 2011/0046436 A1 * | 2/2011 | Sokol | 600/30 |
| 2011/0124956 A1 * | 5/2011 | Mujwid et al. | 600/30 |
| 2011/0230707 A1 * | 9/2011 | Roll et al. | 600/37 |

* cited by examiner

*Primary Examiner* — Charles A Marmor, II
*Assistant Examiner* — Joshua D Lannu
(74) *Attorney, Agent, or Firm* — Brake Hughes Bellermann LLP

(57) ABSTRACT

A method and device for the treatment of fecal incontinence is disclosed. The method includes disposing a bodily implant proximate to an anal canal of a patient. The bodily implant has a strip extending along a length between a first end portion and a second end portion. The strip has a set of first projections and a set of second projections extending along at least a portion of a longitudinal edge of the strip, such that the set of the first projections are inclined toward the second end portion of the strip and the set of the second projections are inclined toward the first end portion of the strip.

9 Claims, 33 Drawing Sheets

BODILY IMPLANTS AND METHODS FOR DELIVERY AND PLACEMENT OF BODILY IMPLANTS INTO A PATIENTS BODY

CROSS-REFERENCE TO RELATED APPLICATION

This application is a Nonprovisional of, and claims priority to, U.S. Patent Application No. 61/568,967, filed Dec. 9, 2011, entitled "DELIVERY AND PLACEMENT OF BODILY IMPLANTS INTO A PATIENT'S BODY", which is incorporated by reference herein in its entirety.

BACKGROUND

1. Field

The invention generally relates to medical devices and procedures, and more particularly to bodily implants and their delivery and placement into a patient's body for the treatment of fecal incontinence.

2. Description of the Related Art

Fecal incontinence is a disorder that involves involuntary passage of feces through an anal canal. The disorder may be caused by the weakness or damage of the internal and external anal sphincter muscles or the levator ani muscles surrounding the anal canal in a human body. The internal and external sphincters and levator ani muscles support a rectum and provide the rectum an ano-rectal angle. The ano-rectal angle sustains feces in the rectum until voluntary defecation relaxes the puborectalis muscle and straightens the angle, allowing the feces to move towards an anus of the human body.

A variety of procedures are performed, including surgical and non-surgical techniques, to treat various disorders and damages of the internal and external anal sphincter muscles or the levator ani muscles surrounding the anal canal. One of the surgical treatments includes a sling procedure involving an implant or bodily implants such as slings into a patient's body around the anal canal. New kinds of synthetic materials for the slings and procedures for their implant have been used in the past few years.

Depending on the particular condition of fecal incontinence to be treated and the kind of devices used for surgery, slings may be placed at various specific anatomical locations surrounding the rectum or anal canal. Accordingly, incisions are made for puncturing the skin to deliver the sling inside the body tissues. The existing sling procedures involve implantation using multiple incisions such as three, four or even more. Delivery of some slings includes perineal or vaginal incisions as well.

Various complications can occur during a surgical sling procedure to deliver and secure the sling around the rectum through multiple incisions and specifically around a fragile area near the perineum and vagina. Dissection of the fragile area through multiple incisions may damage the surrounding parts and may even result in severe post-surgery complications leading to even removal or replacement of the sling.

In addition, the currently available designs of slings and their placement for the treatment of anal incontinence may find difficulties in their engagement and proper tensioning with the body tissues.

In accordance with the foregoing, there is a need for devices and methods for facilitating delivery and placement of the slings around the anal canal for the treatment of fecal incontinence.

SUMMARY

A method and device for the treatment of fecal incontinence is disclosed. The method includes disposing a bodily implant proximate to an anal canal of a patient. The bodily implant has a strip extending along a length between a first end portion and a second end portion. The strip has a set of first projections and a set of second projections extending along at least a portion of a longitudinal edge of the strip, such that the set of the first projections are inclined toward the second end portion of the strip and the set of the second projections are inclined toward the first end portion of the strip. The set of the first projections is secured to a first portion of body tissue such that the set of the first projections allows movement of the bodily implant with respect to the first portion of the body tissue in a first direction and restricts movement of the bodily implant with respect to the first portion of the body tissue in a second direction. The set of the second projections is secured to a second portion of the body tissue such that the set of the second projections allows movement of the bodily implant with respect to the second portion of the body tissue in the second direction and restricts movement of the bodily implant with respect to the second portion of the body tissue in the first direction.

BRIEF DESCRIPTION OF THE FIGURES

The invention and the following detailed description of certain embodiments thereof may be understood by reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

The present invention relates to devices and methods for delivery and placement of bodily implants into a patient's body for the treatment of fecal incontinence. In some embodiments, the bodily implants act as anal supports and facilitate in proper tensioning of internal and external anal sphincter muscles or the levator ani muscles surrounding the anal canal to prevent involuntary passage of feces. In some embodiments, the anal support provided by the bodily implants involves formation of a loop structure around the anus that applies a tensioning force to maintain the sphincters in a position that is more desired for preventing the involuntary passage of feces. In some embodiments, the bodily implants are fixed by adjacent scar tissues upon healing.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like who may perform the procedure of delivery and placement of the bodily implants into the patient's body as described in the present invention. The term proximal refers to an area that is closest to the operator. The term distal refers to an area that is farthest from the operator. The patient may be a human female, a human male or any other mammal.

Figure 1:
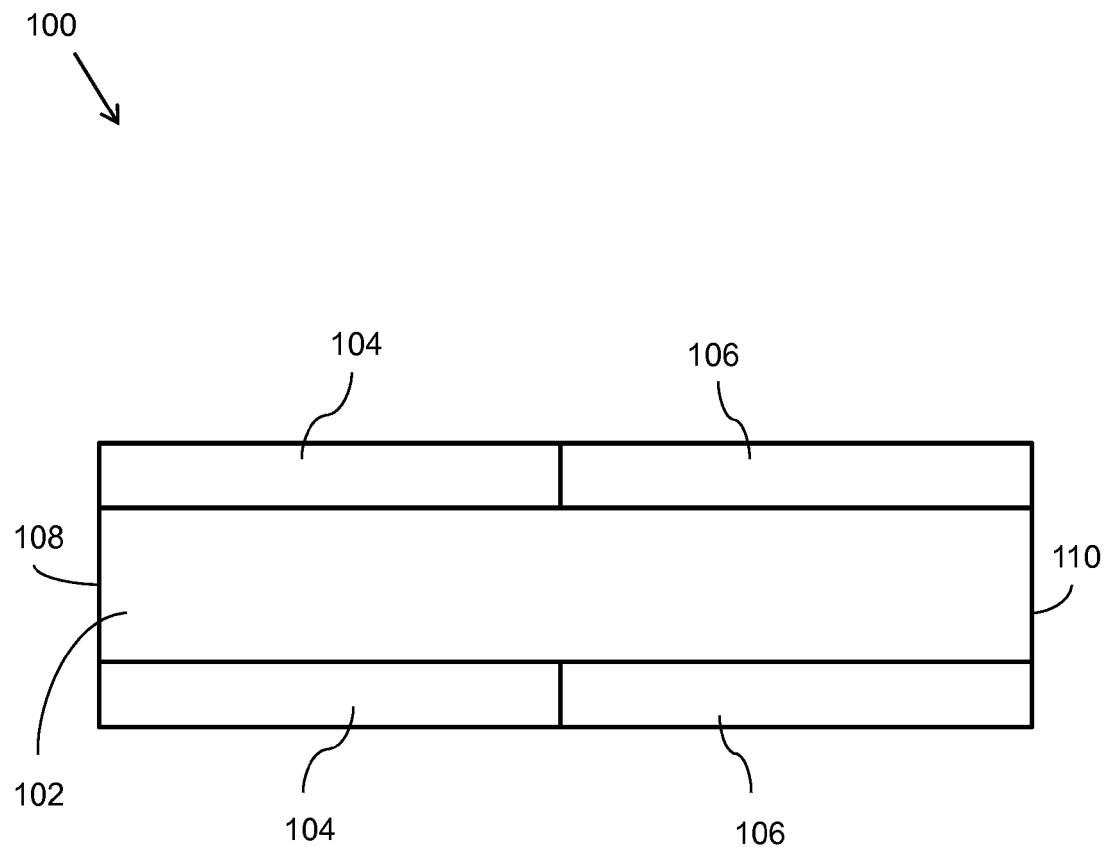
FIG. 1 is a schematic diagram of a bodily implant configured to be delivered into a patient's body for the treatment of fecal incontinence, in accordance with an embodiment of the present invention.

FIG. 1 is an illustration of a bodily implant 100 configured to be delivered into a patient's body for the treatment of fecal incontinence in a first configuration, according to an embodiment of the present invention. The bodily implant 100 may be a sling system that is utilized in the treatment of urinary and/or fecal incontinence. The bodily implant 100 includes a strip 102, a first set of projections 104, and a second set of projections 106.

The strip 102 is configured to be placed within the patient's body and support a portion of the body. The strip 102 has a first end portion 108 and a second end portion 110 such that the strip 102 extends along a length between the first end portion 108 and the second end portion 110. The length and width of the strip 102 may vary based on the intended use of the bodily implant 100. The strip 102 can be of a variety of sizes, shapes, and configurations depending on the intended use and locations of placement of the bodily implant 100. The strip 102 can be shaped and sized to support a portion of the body around an anal canal, or a rectum, or an anus of the patient. In accordance with various embodiments, the strip 102 may extend linearly along an entire length between the first end portion 108 and the second end portion 110. In other embodiments of the present invention, the strip 102 may include a support member disposed on a portion of the strip 102. The support member may be of different shapes such as rectangular, oval, circular, elliptical, and the like.

In some embodiments, the strip 102 is formed of a material that allows tissue ingrowth after implantation. Various types of woven tapes, fabrics, meshes, or single or multiple fibers may be utilized in the fabrication and manufacturing of the strip 102, in accordance with various embodiments of the present invention. The strip 102 may utilize a variety of mesh materials and may be designed in a variety of forms. An example of a mesh utilized in the strip is Polyform® Synthetic Mesh developed by the Boston Scientific Corporation. The Polyform® Synthetic Mesh is made from uncoated monofilament macro-porous polypropylene. The strip 102 may also be made from a biological material or a cadaveric tissue. Typically, the strip 102 has a smooth surface to avoid or reduce irritation on adjacent body tissues during mesh-tissue interactions. Additionally, the strip 102 may be stretchable and flexible to adapt movements in accordance with the anatomy of the human body and reduce suture pullout. Furthermore, softness, lightness, conformity, and strength are certain other attributes required in the strip 102 for efficient tissue repair and implantation. In an embodiment, the strip 102 can have a coating. For example, the strip 102 can be coated with an antimicrobial agent and/or an antifungal agent.

The set of the first projections 104 and the set of the second projections 106 extend along at least a portion of longitudinal edges of the strip 102. The set of the first projections 104 is inclined toward the second end portion 110 of the strip 102 and the set of the second projections 106 is inclined toward the first end portion 108 of the strip 102. The set of the first projections 104 and the set of the second projections 106 are configured to engage with tissues of the anal canal upon delivery and placement of the bodily implant 100 around the anal sphincters or canal.

In some embodiments, the set of the first projections 104 and the set of the second projections 106 are formed with the same material as the strip 102. In certain other embodiments, the set of the first projections 104 and the set of the second projections 106 are formed with a different material than the strip 102. For example, the set of the first projections 104 and the set of the second projections 106 can be formed with a first biocompatible material and the strip 102 can be formed with a second biocompatible material different than the first biocompatible material. In some embodiments, the material of the set of the first projections 104 and the set of the second projections 106 may also be different. For example, the set of the first projections 104 may be manufactured from a first biological material and the set of the second projections 106 may be manufactured from a second biological material different than the first biological material.

In some embodiments, the profiles or shapes of the set of the first projections 104 and the set of the second projections 106 may be same. In other embodiments, the profiles or shapes of the set of the first projections 104 and the set of the second projections 106 may be different. In accordance with various embodiments of the present invention, the profiles or shapes of the set of the first projections 104 and the set of the second projections 106 may vary depending on the requirements. The profiles may include, without limitations, linear, circular, triangular, elliptical, hyperboloid, parabolic, involute, and the like.

In some embodiments, the set of the first projections 104 and the set of the second projections 106 may be integrally formed with the strip 102. In other embodiments, the set of the first projections 104 and the set of the second projections 106 may be removably coupled or tied to the strip 102.

In some embodiments, the set of the first projections 104 and the set of the second projections 106 may be provided along one longitudinal edge of the strip 102. In some other embodiments, the set of the first projections 104 and the set of the second projections 106 may be provided along both longitudinal edges of the strip 102. The size and shape of the strip 102 and the set of the first projections 104 and the set of the second projections 106 in the first configuration as illustrated in FIG. 1 is merely exemplary, and various other shapes and sizes are possible without limiting the spirit and scope of the present invention.

Figure 2:
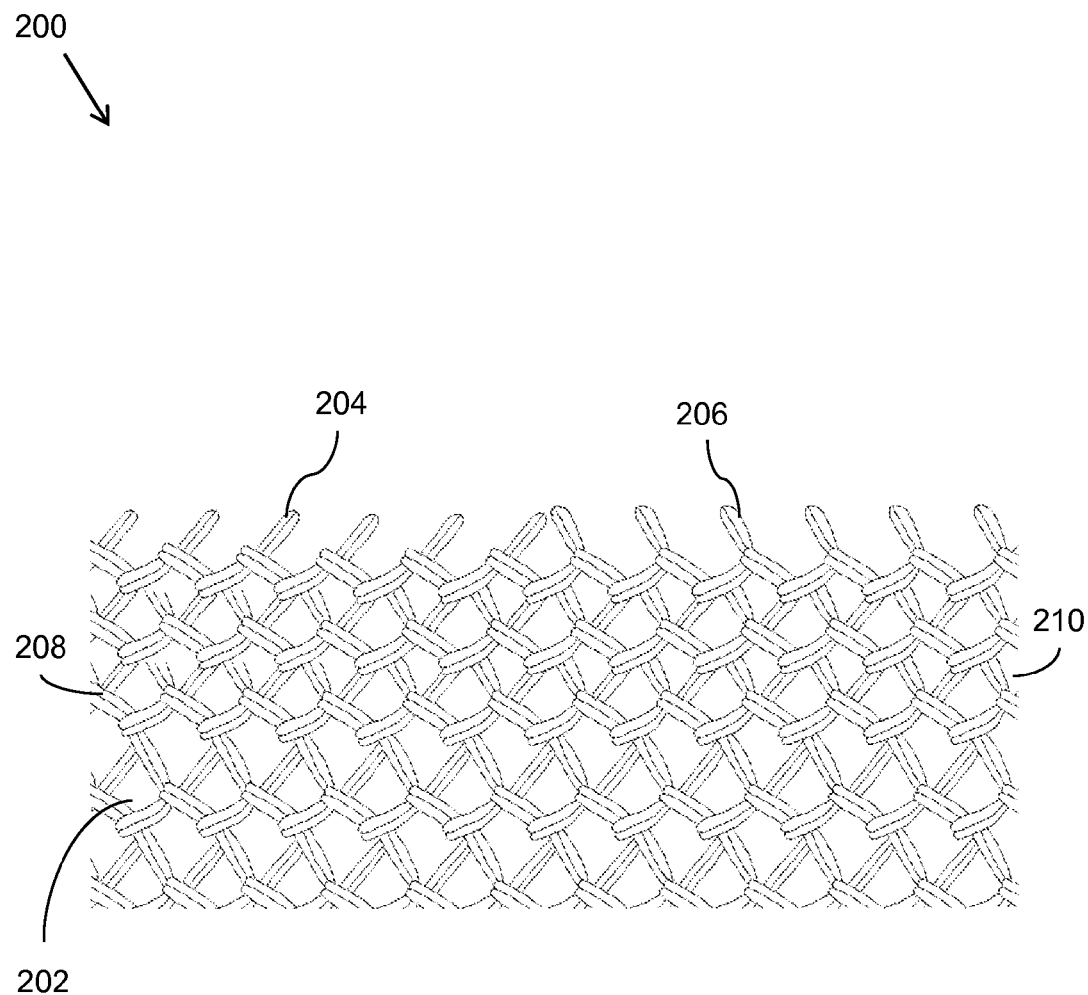
FIG. 2 is a perspective illustration of a section of a bodily implant according to an embodiment of the invention.

FIG. 2 is a perspective illustration of a section of a bodily implant 200, in accordance with an embodiment of the present invention. The bodily implant 200 includes a strip 202 having an array of cells interlocked across a width and along a certain length of the strip 202. The number of cells may vary across the width and along the length of the strip 202 depending on the intended use and the dimensions of the damage or tear. In certain embodiments, the bodily implant 200 may include multiple interwoven strands or fibers that collectively form the interlocked structure of the array of cells. The bodily implant 200 can be formed of a knitted, woven or non-woven matrix, and the like. In some embodiments, the bodily implant or mesh may utilize single filament or fiber (such as in a monofilament structure). In other embodiments, the bodily implant or mesh may be formed of multiple fibers or filaments. The fibers or filaments, in this case, may be same or may differ in properties such as strength, elasticity, flexibility, degradation time value and the like.

The bodily implant 200 acts as a support for tensioning around the anal canal as well as a suture that may be used for closing a tear or wound or damage. This may be especially used in cases of torn sphincters or other torn tissues. The surgical procedure to secure the bodily implant 200 with the body tissues and to close the tear or wound is described in detail in conjunction with FIG. 18. In accordance with some embodiments, one or more elongated arms (not shown) may be tied or coupled to the strip 202 that facilitate in stability and retention of the bodily implant 200 with the body tissues. The elongated arms may be fixed at various anatomical locations inside the patient's body. The shape and size of the elongated arms may vary based on the intended use and the location of its placement. In some embodiments, the material of the elongated arms and the strip 202 may be same. In other embodiments, the material of the elongated arms and the strip 202 may be different. Further, in certain embodiments, the elongated arms may be removably tied to the strip 202. In alternative embodiments, the elongated arms may form an integral part of the strip 202 such that the strip 202 together with the elongated arms constitutes the bodily implant 200.

Figure 3:
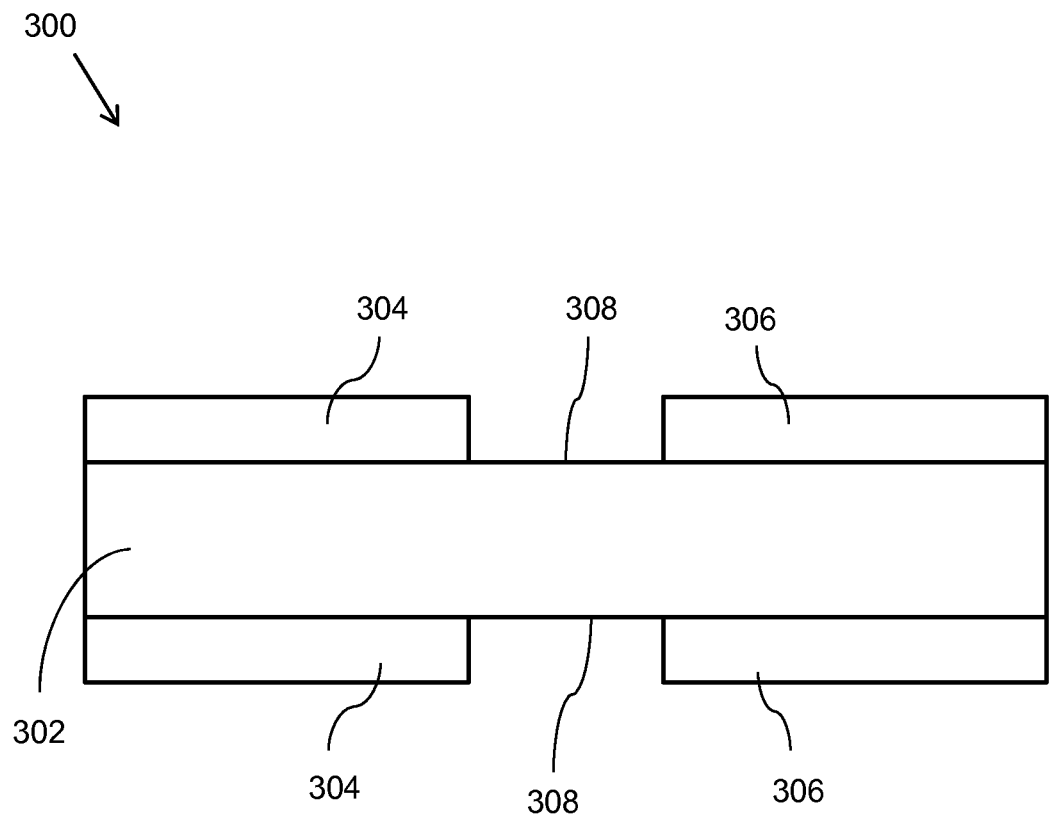
FIG. 3 is a schematic diagram of a bodily implant configured to be delivered into a patient's body for the treatment of fecal incontinence, in accordance with an embodiment of the present invention.

FIG. 3 is an illustration of a bodily implant 300 configured to be delivered into the patient's body for the treatment of fecal incontinence in a second configuration, according to an embodiment of the present invention. In accordance with this configuration, the bodily implant 300 includes a strip 302, a set of first projections 304, and a set of second projections 306. The strip 302 further includes a projectionless portion (or a portion that is relatively smooth or devoid of projections) 308 between the set of the first projections 304 and the set of the second projections 306. The projectionless portion 308 is configured to surround or extend between the tear or damage (or ends thereof) proximate to the anal canal or the anal sphincter of the patient. In accordance with various embodiments, the length of the projectionless portion 308 across the length of the strip 302 may vary depending on the length of the tear or damage around or proximate to the anal canal, or rectum, or anus, or sphincter muscles, and the like. In some embodiments, the projectionless portion 308 is provided at the central part of the strip 302. In other embodiments, the projectionless portion 308 is shifted more toward one of the end portions of the strip 302. The size and shape of the strip 302, the set of the first projections 304, and the set of the second projections 306 in the second configuration as illustrated in FIG. 3 is merely exemplary, and various other shapes and sizes are possible without limiting the spirit and scope of the present invention. In some embodiments, the bodily implant 300 or the strip 302 do not include any projections. In other words, the bodily implant 300 is relatively smooth from one end of the strip 302 to the opposite end of the strip 302.

Figure 4:
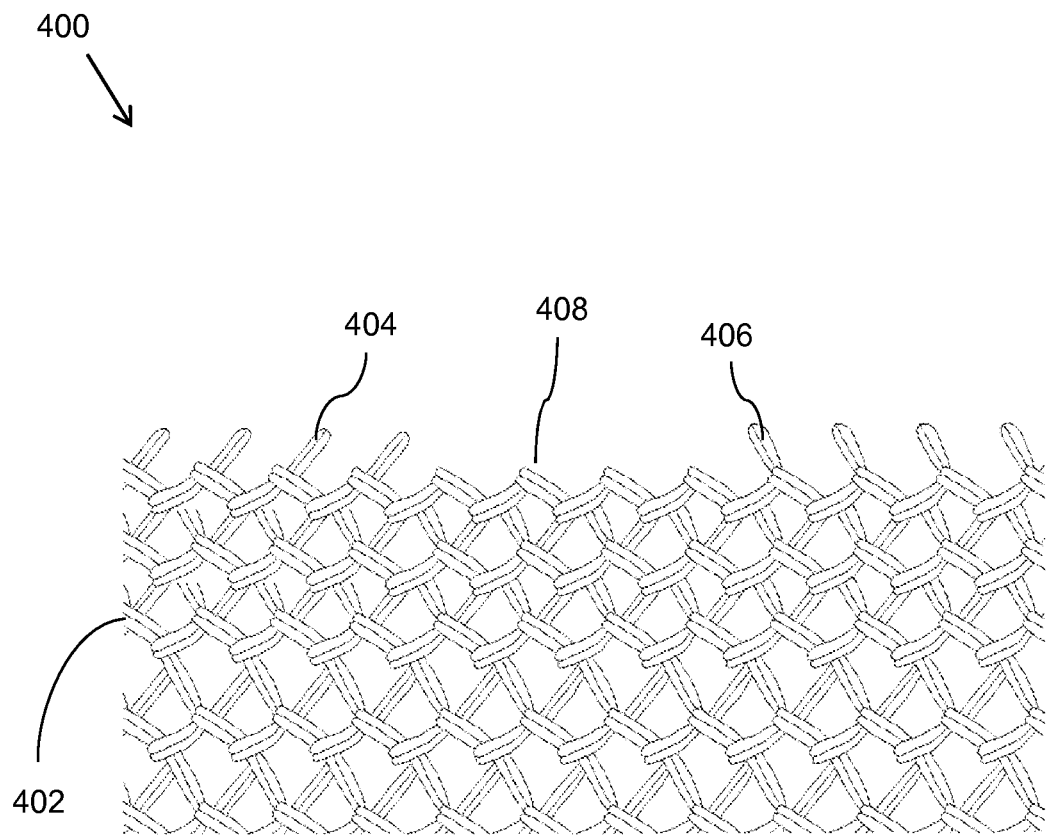
FIG. 4 is a perspective illustration of a section of a bodily implant according to an embodiment of the invention.

FIG. 4 is a perspective illustration of a section of a bodily implant 400 in the second configuration, in accordance with an embodiment of the present invention. The bodily implant 400 includes the strip 402 having an array of cells interlocked across a width and along a certain length of the strip 402. The number of cells may vary across the width and the length of the strip 402 depending on the intended use and the dimensions of the damage or tear.

Figure 5:
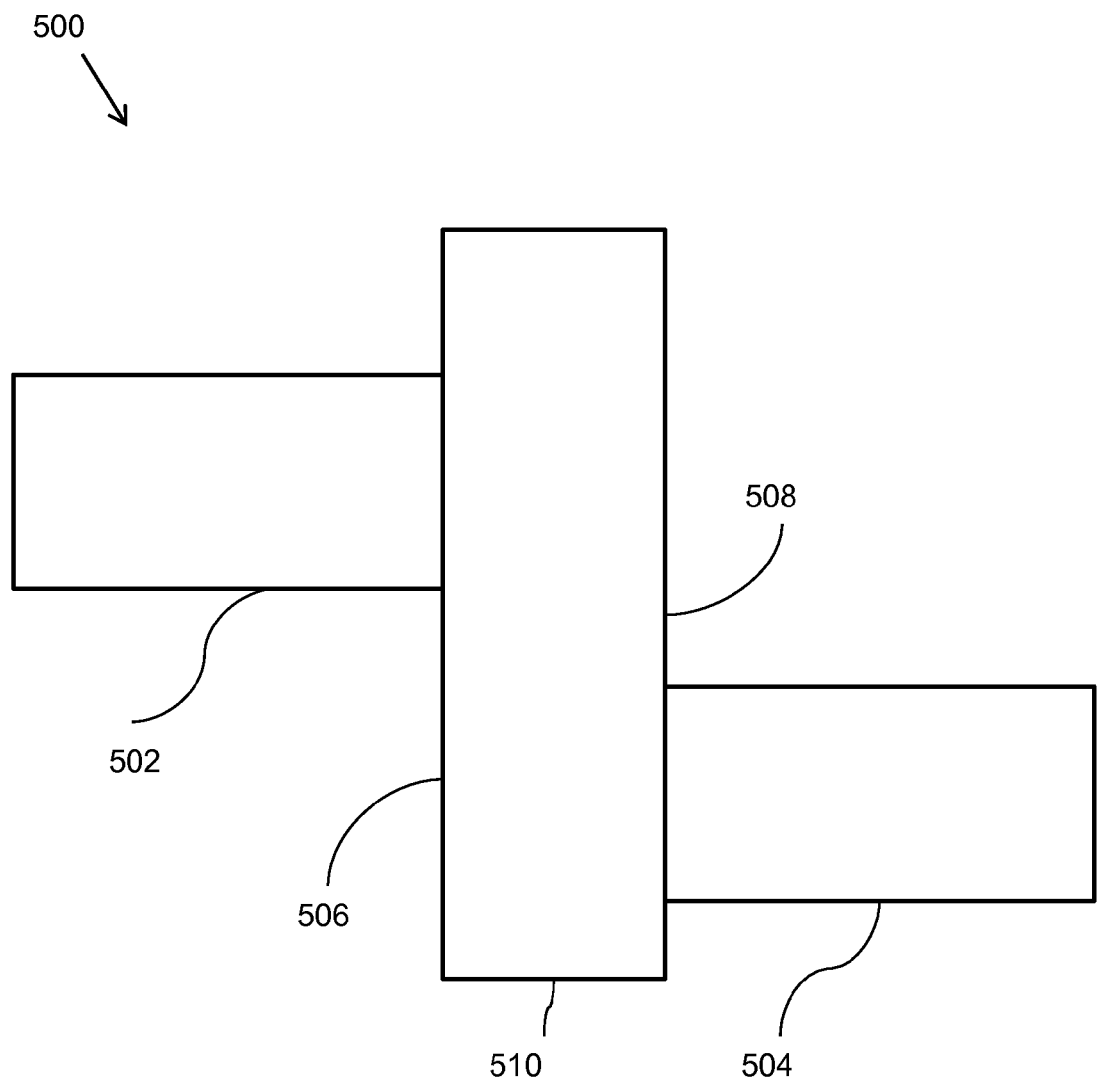
FIG. 5 is a schematic diagram of a device configured to be delivered into a patient's body for the treatment of fecal incontinence, in accordance with another embodiment of the present invention.

FIG. 5 is an illustration of a device 500 configured to be delivered into the patient's body for the treatment of fecal incontinence, according to an embodiment of the present invention. The device 500 includes a first member 502 and a second member 504. The first member 502 has two end portions and a middle portion disposed between the two end portions. The middle portion of the first member 502 is configured to surround or be disposed adjacent a first side 506 of an anal canal 510 of the patient. In an exemplary scenario, the first side 506 is an anterior side of the anal canal 510. The middle portion of the first member 502 acts as a support on the first side 506 of the anal canal 510. In some embodiments, the anal support provided by the first member 502 involves formation of a loop or sling structure around the anterior part of the anal canal 510. The two end portions of the first member 502 can be used to fix in place within body tissues.

The second member 504 has two end portions and a middle portion disposed between the two end portions. The middle portion of the second member 504 is configured to surround or be disposed adjacent a second side 508 of the anal canal 510. In an exemplary scenario, the second side 508 is a posterior of the anal canal 510. The middle portion of the second member 504 acts as a support on the second side 508 of the anal canal 510. The anal support provided by the second member 504 involves formation of a loop or sling structure around a posterior side or part of the anal canal 510. The two end portions of the second member 504 can be used to fix within body tissues. In some embodiments, the second side 508 is substantially opposite to the first side 506 and the second member 504 is spaced longitudinally along the anal canal from the first member 502 as illustrated in FIG. 5. The placing of the first member 502 and the second member 504 in this manner provide two substantially semi-circular loop structures on two opposite sides of the anal canal 510 such that the loop structures are longitudinally placed apart by a fixed distance. The fixed distance may be a few inches as preferred by the operator depending on the intended use of placement of the device 500.

In accordance with an embodiment, the first member 502 and the second member 504 are bodily implants. In some embodiments, at least one of the first member 502 and the second member 504 is similar to the bodily implants as illustrated in FIGS. 1-4. Specifically, in some embodiments, the at least one of the first member 502 and the second member 504 can be the bodily implant as illustrated in FIGS. 1 and 2. In some other embodiments, the at least one of the first member 502 and the second member 504 can be the bodily implant as illustrated in FIGS. 3 and 4. Therefore, in some embodiments, at least one of the first member 502 and the second member 504 includes the strip 102 extending along the length between the first end portion 108 and the second end portion 110. The strip 102 has the set of the first projections 104 and the set of the second projections 106 extending along at least a portion of longitudinal edges of the strip 102. The set of the first projections 104 are inclined toward the second end portion 110 of the strip 102 and the set of the second projections 106 are inclined toward the first end portion 108 of the strip 102.

The first member 502 and the second member 504 can be of a variety of different sizes, shapes, and configurations depending on the intended use and locations of placement of the device 500. The first member 502 and the second member 504 can be shaped and sized to support a portion of the body around the anal canal, the rectum, or the anus of the patient. In some embodiments, the shape, size, and/or configuration of the first member 502 and the second member 504 may be same. In some other embodiments, the shape, size, and/or configuration of the first member 502 and the second member 504 may be different.

In some embodiments, the first member 502 and the second member 504 are formed of a material that allows tissue ingrowth after implantation. Various types of woven tapes and fabrics may be utilized in the fabrication and manufacturing of the first member 502 and the second member 504, in accordance with various embodiments of the present invention, similar to the bodily implants described in conjunction with FIGS. 1-4. The size and shape of the first member 502 and the second member 504 (as illustrated in FIG. 5) is merely exemplary, and various other shapes and sizes are possible without limiting the spirit and scope of the present invention.

In some embodiments, the first member 502 and the second member 504 are formed with the same material. In certain other embodiments, the first member 502 and the second member 504 are formed from a different material. For example, the first member 502 can be formed with a first biocompatible material and the second member 504 can be formed with a second biocompatible material different than the first biocompatible material.

Figure 6:
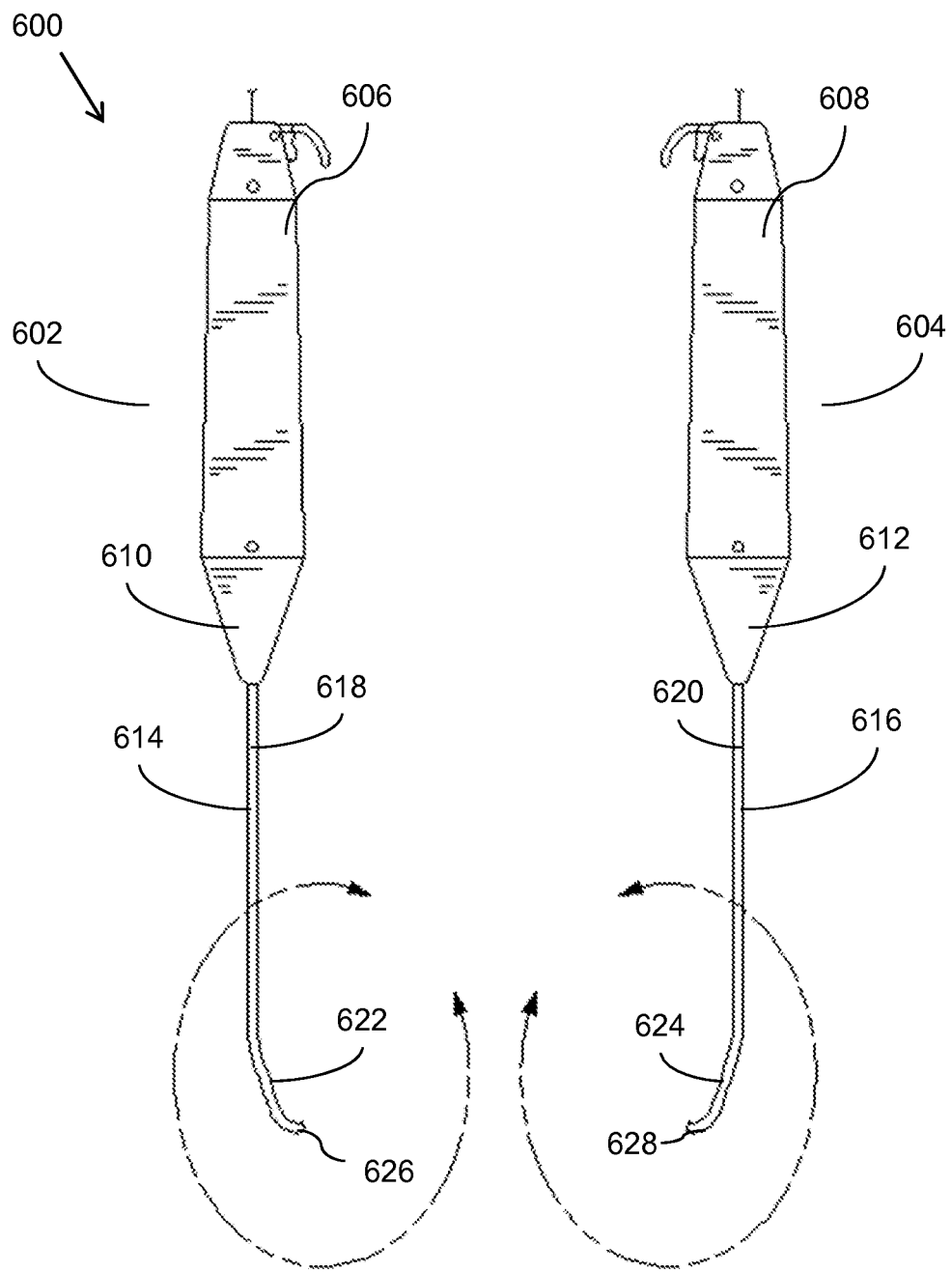
FIG. 6 is a front view illustration of a medical device having a first trocar and a second trocar, in accordance with an embodiment of the present invention.
Figure 7A:
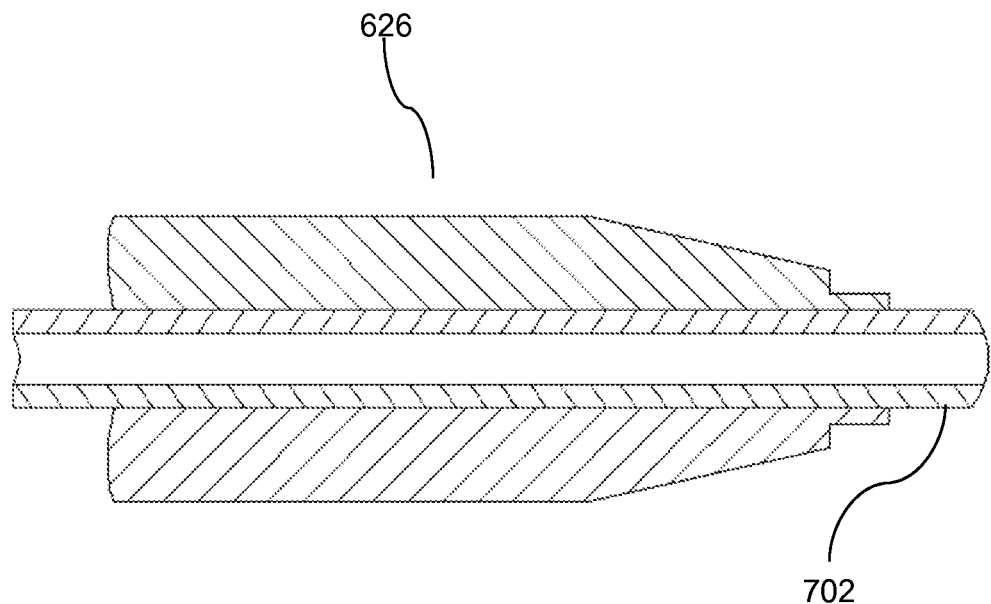
FIGS. 7A and 7B illustrate a cross-sectional view of a distal end of the first trocar and a distal end of the second trocar, respectively.
Figure 7B:
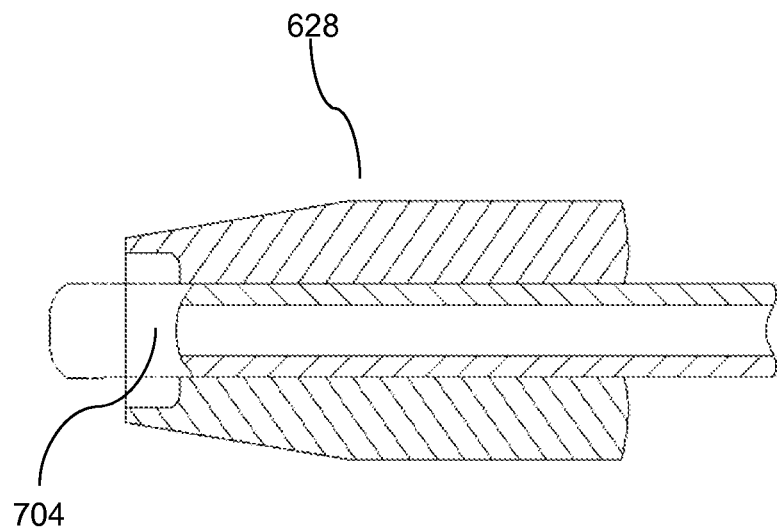

Referring to FIG. 6, there is disclosed a medical device 600 configured to deliver an implant, such as bodily implant 100 inside the patient's body in accordance with various embodiments of the present invention. The medical device 600 includes a first trocar 602 and a second trocar 604 having handles 606 and 608, respectively to serve as gripping members and as support for the medical device 600. In some embodiments, the handles 606 and 608 have hollow tubular body. A hollow support portion 610 is coupled at a distal end of the handle 606 and a similar support portion 612 is coupled at a distal end of the handle 608. Elongated members 614 and 616 extending in the form of shafts are coupled to the support portions 610 and 612 with their proximal ends inserted in the support portions 610 and 612 and the distal ends extending away from the support portions 610 and 612 respectively. The elongated members 614 and 616 may be removably coupled to the support portions 610 and 612 or permanently coupled through techniques such as welding, soldering, and the like. The elongated members 614 and 616 have lumen defined therein and extending along the length of the elongated members 614 and 616. In other embodiments, the elongated members 614 and 616 may be solid in nature. In accordance with an embodiment, the elongated members 614 and 616 have straight proximal portions 618 and 620, bent intermediate portions 622 and 624, and distal end portions 626 and 628, respectively. As illustrated in FIGS. 7A and 7B, the distal end portions 626 and 628 of the elongated members 614 and 616 of the medical device 600 are provided with engaging members 702 and 704 that are complementary to each other, such that the elongated members 614 and 616 of the two trocars 602 and 604 are adapted to be attached to one another. An example of such a medical device is described in U.S. Pat. No. 6,423,080, the disclosure of which is hereby incorporated by reference in its entirety. In some embodiments, the distal end portion 628 can include a flexible obturator that is slidably disposed in the hollow lumens of the trocars 602 and 604 to guide the device through tissue and aid in the alignment and/or coupling of engaging members 702 and 704.

Figure 8A:
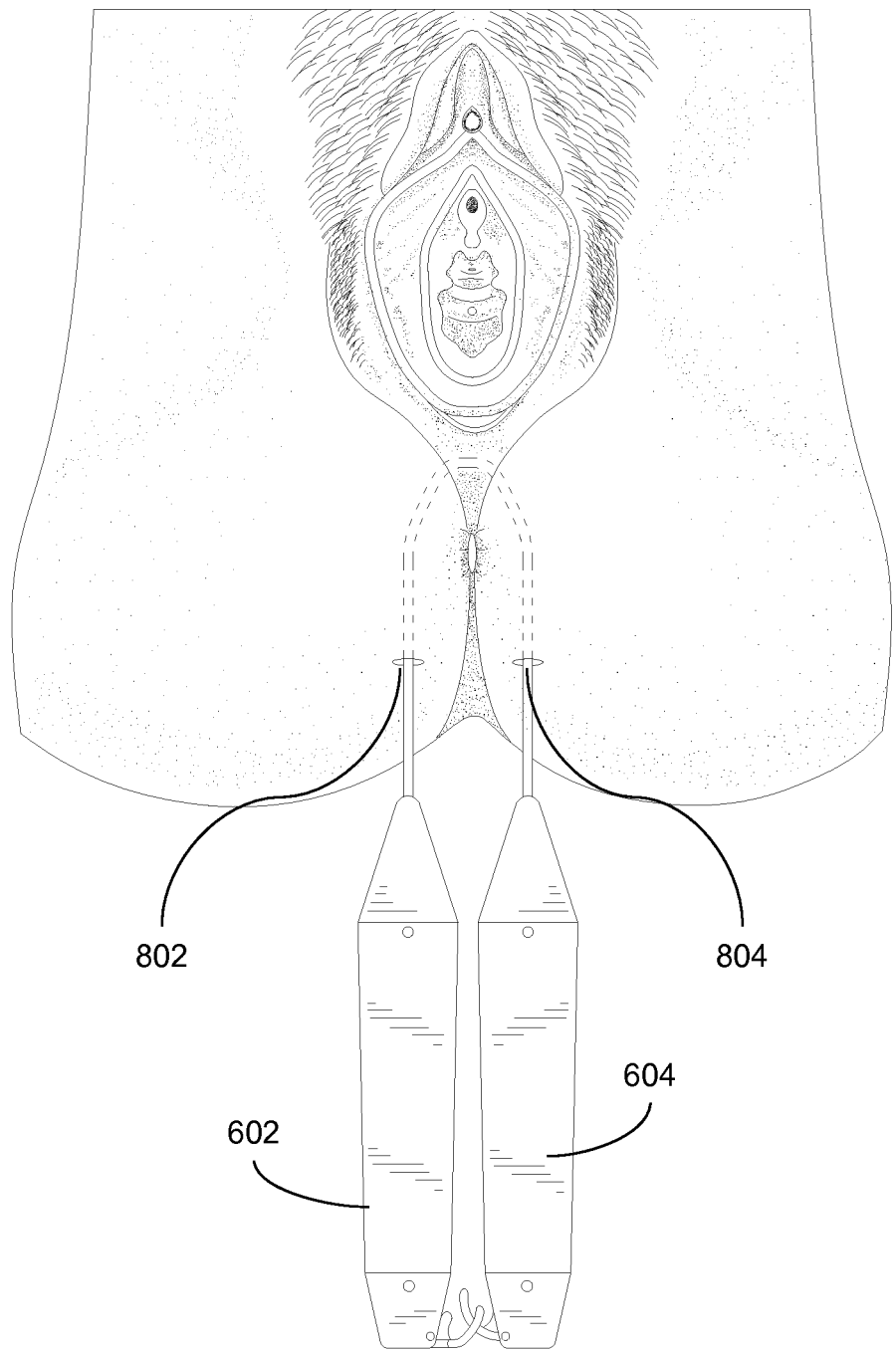
FIGS. 8A-8D illustrate a medical device delivering a bodily implant into a patient's body, in accordance with an embodiment of the present invention.
Figure 8B:
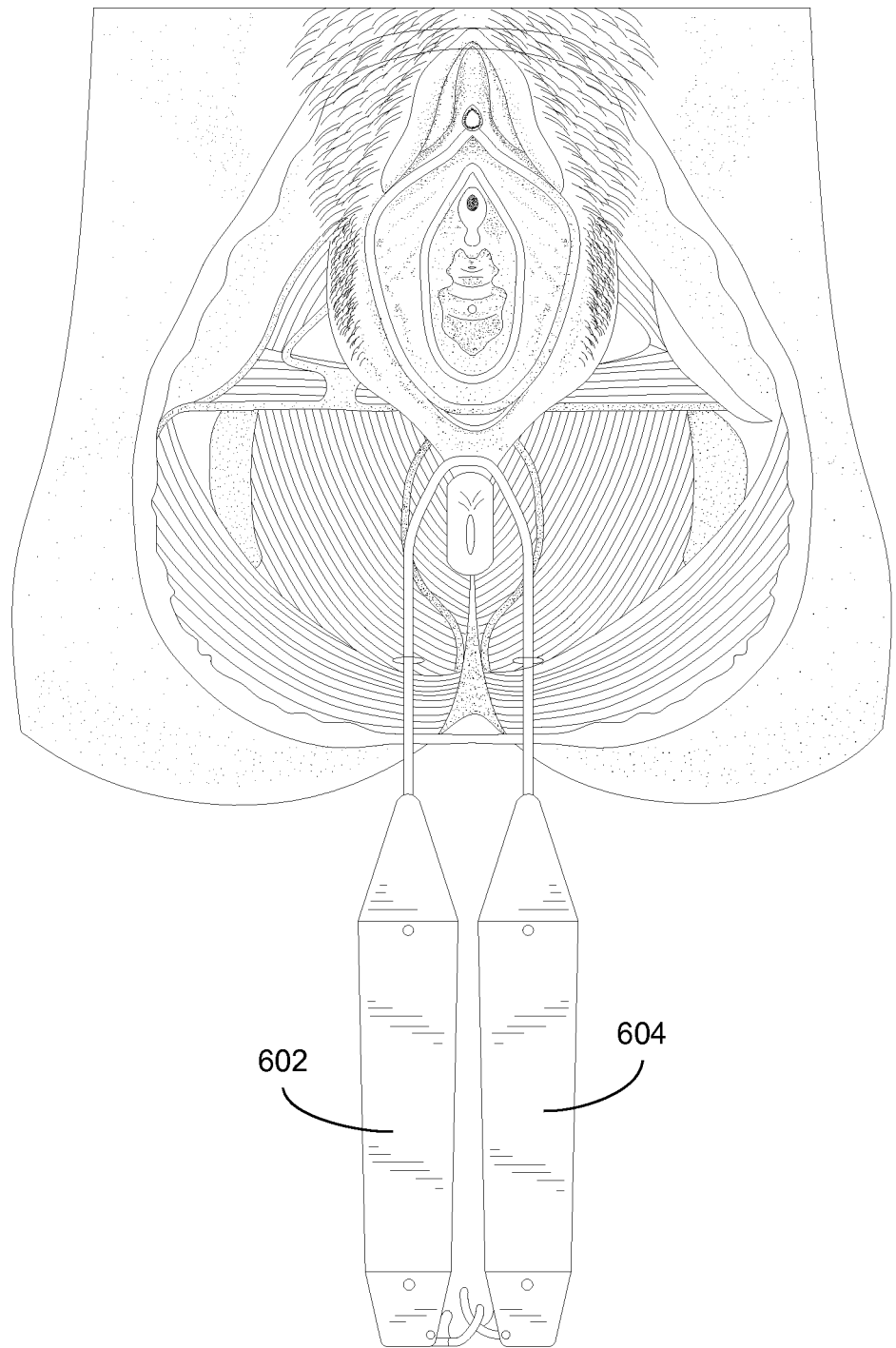
Figure 8C:
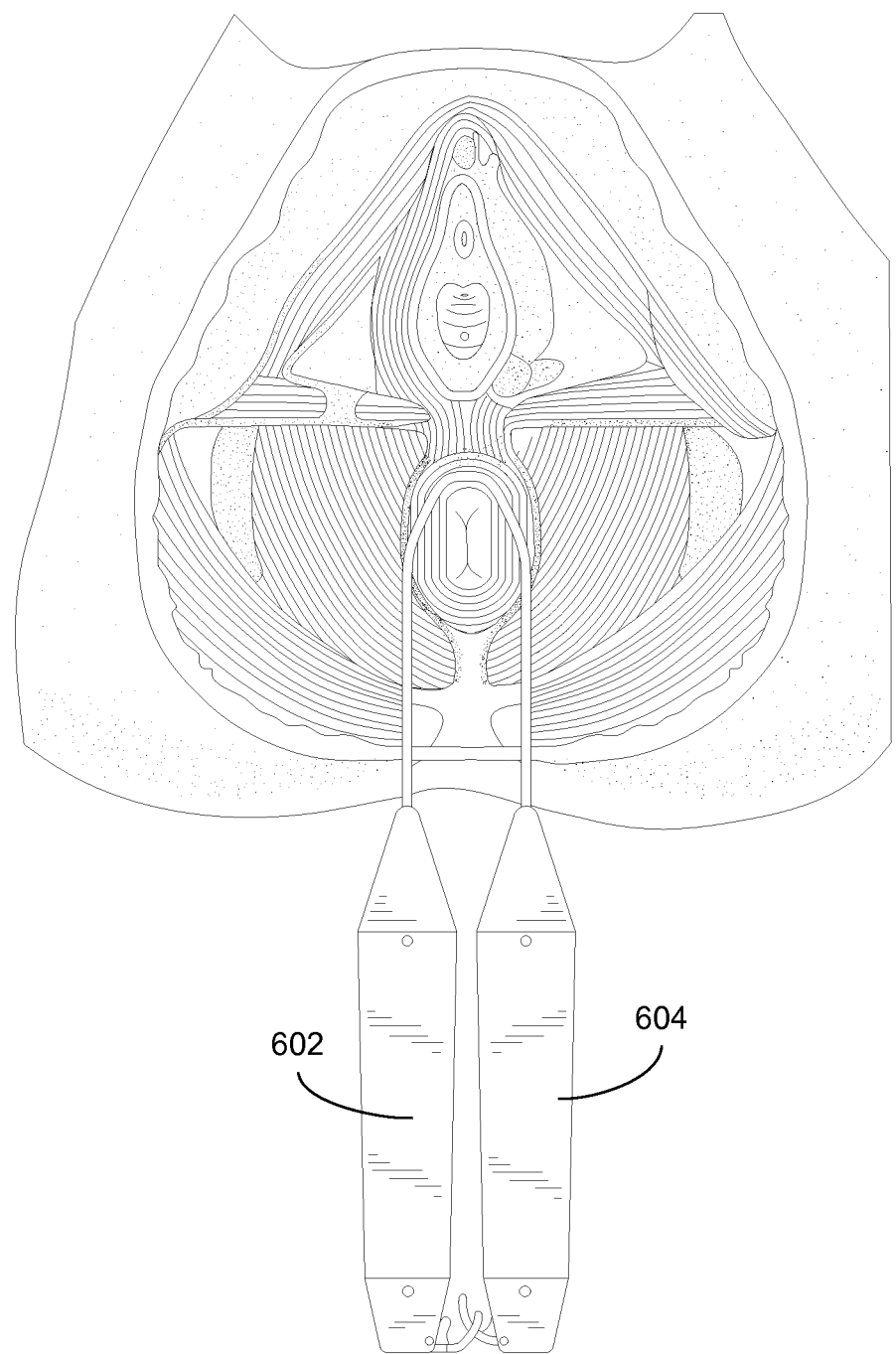
Figure 8D:
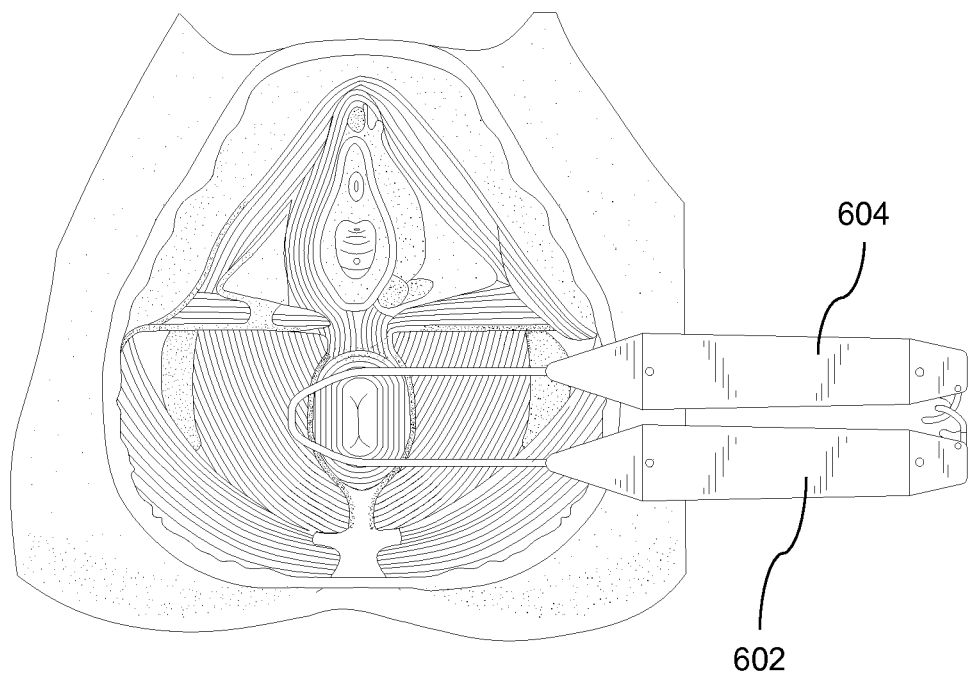

Referring to FIG. 8A, FIG. 8B, FIG. 8C, and FIG. 8D, there is disclosed an illustration of delivery of a bodily implant such as the bodily implant 100 into the patient's body with the use of the medical device 600, in accordance with an embodiment of the present invention. The delivery and placement of the bodily implant 100 is shown in a female anatomical structure. Though in other embodiments, the bodily implant may be placed within a male patient. As depicted, the bodily implant 100 is delivered and implanted around the anal canal of the patient with the use of two skin incisions, i.e., a first incision 802 and a second incision 804. In the illustrated embodiment, a third skin incision is not made in the patient. The two incisions 802 and 804 are made in a location posteriorlateral to the anal canal (in other words the location is posterior and lateral to the anal canal or anus). As illustrated in FIGS. 8A, 8B, and 8C, the two trocars of the medical device 600 may be inserted through the skin incisions, through a fat layer or other tissue layer, and into the anal sphincter muscles or other tissue proximate the anal canal of the patient. In the illustrated embodiment, the trocars are placed within the body of the patient such that they collectively extend from the skin incisions and around a portion of the anal canal to form a passageway extending from the first skin incision to the second skin incision. As illustrated in FIGS. 8D, the two trocars of the medical device 600 may be inserted through incisions at a substantially lateral location to the anal canal.

Figure 9A:
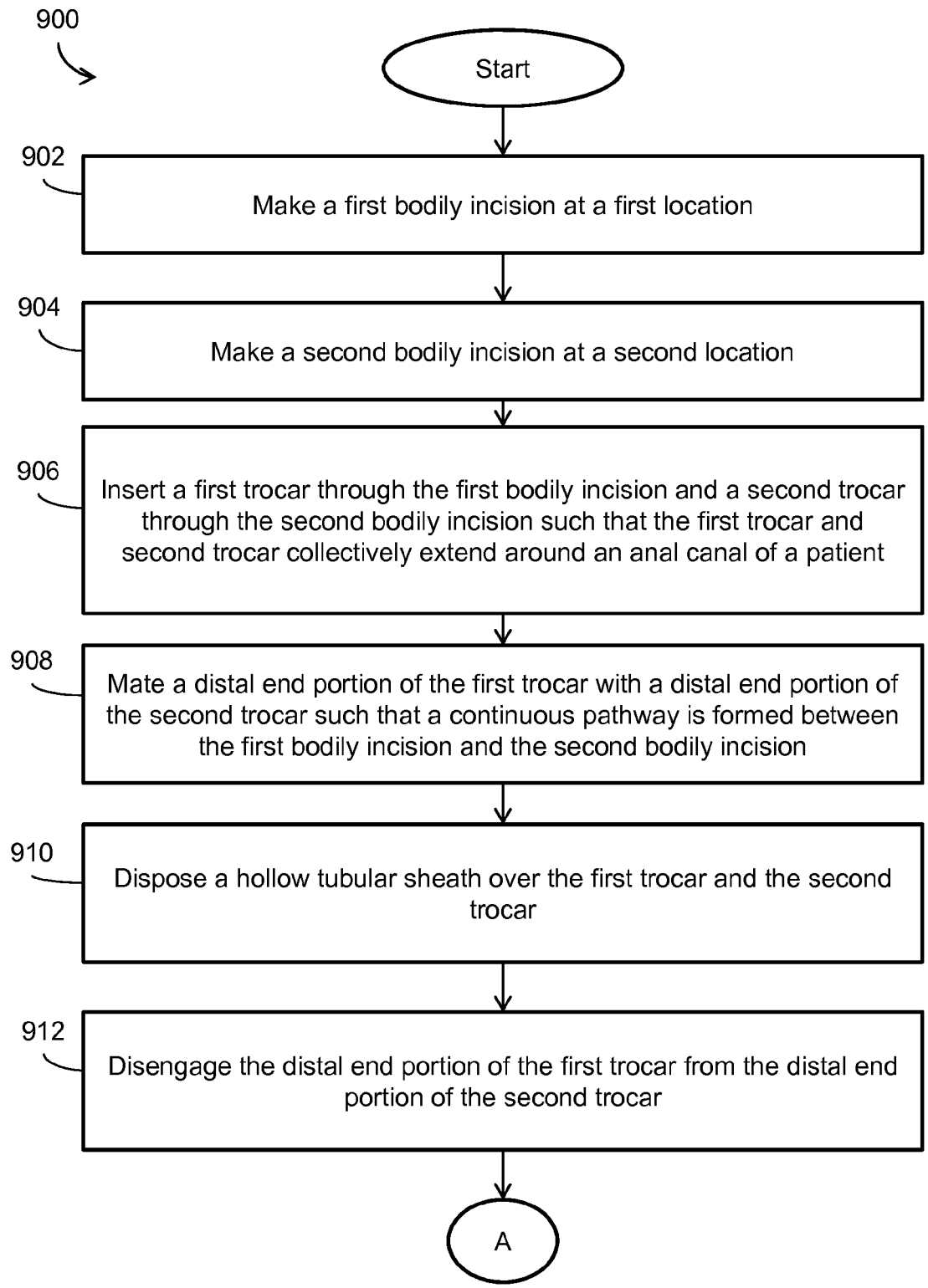
FIGS. 9A-9B is a flowchart illustrating a method of delivery and implant of the bodily implant, in accordance with an embodiment of the invention.
Figure 9B:
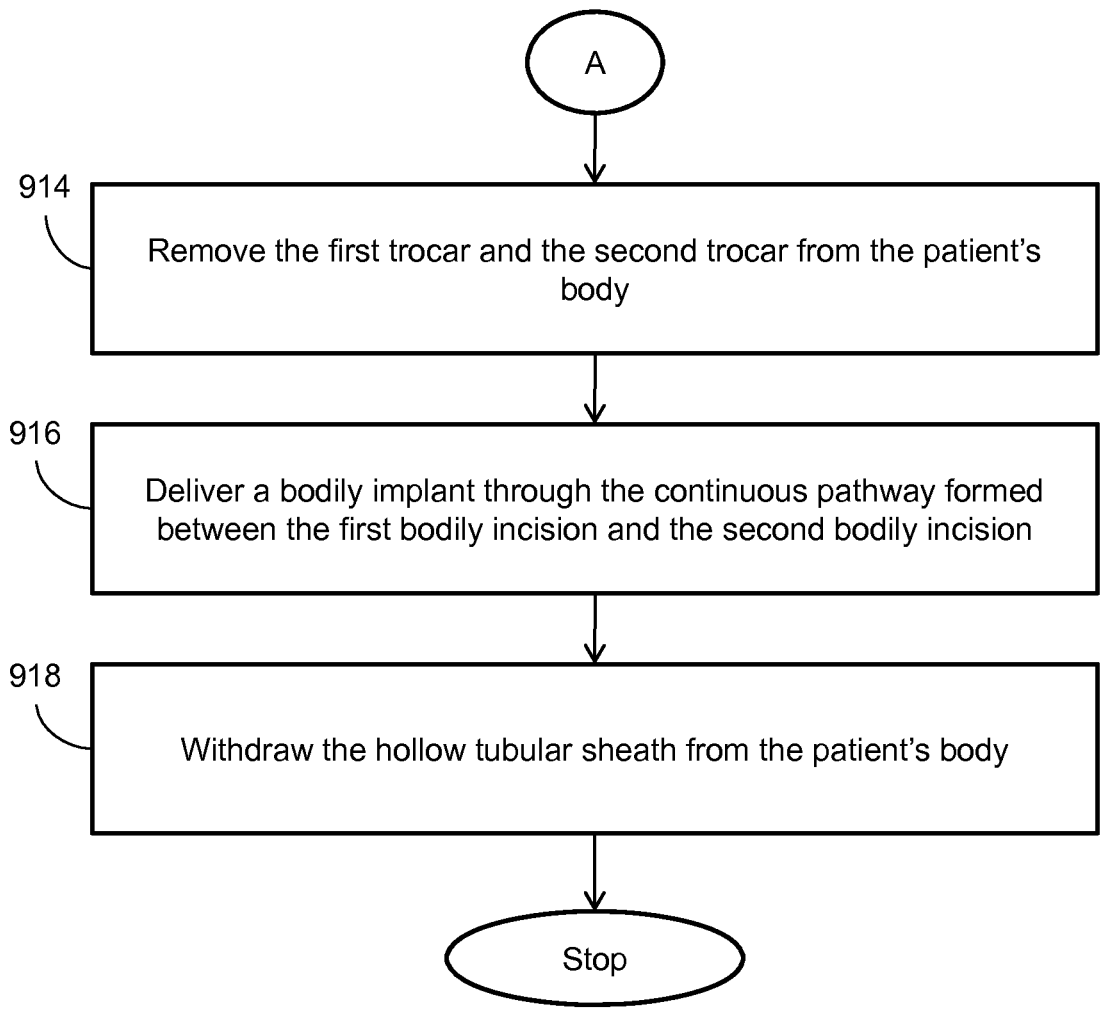

FIGS. 9A and 9B is a flowchart illustrating a method 900 of delivery and implant of bodily implants such as the bodily implant 100, in accordance with an embodiment. As illustrated in FIGS. 9A and 9B, the method 900 includes making a first bodily incision 802 at a first location, at step 902. The first bodily incision is made at a substantially posteriorlateral location to the anus. The first bodily incision may be made with the use of the medical device 600, or scalpel, as described in conjunction with FIG. 6 having the trocars 602 and 604, wherein any of the two trocars 602 and 604 may be used for making the first bodily incision. Essentially, the first bodily incision lies on the right side of the buttock.

At step 904, a second bodily incision is made at a second location different than the first location. The second bodily incision may be made at the substantially posteriorlateral location to the anus but on the opposite side. The second bodily incision is also made in a manner similar to the first bodily incision with the use of the trocars 602 and 604, or scalpel. Essentially, the second bodily incision lies on the left side of the buttock. As illustrated, the first bodily incision and the second bodily incision lie on a substantially same horizontal plane, thereby creating two distinct locations for guiding the medical device 600 therein. In accordance with another embodiment, the first bodily incision and the second bodily incision may be made on locations substantially anteriolateral to the anus (in other words, locations that are anterior and lateral to the anal canal or anus of the patient). For example, in this scenario, the two bodily incisions lie on the right and left sides of the perennial body. In still another embodiment, the two bodily incisions may be made on lateral positions with respect to the anus (lying on left buttock or right buttock).

At step 906, the first trocar 602 is inserted through the first bodily incision and the second trocar 604 is inserted through the second bodily incision such that the first trocar and second trocar collectively extend around an anal canal of a patient and such that a continuous pathway is formed between the first bodily incision and the second bodily incision. The trocars 602 and 604 can be directed to proper body tissues or tissue planes by manual transanal or transcutaneous palpation and/or transanal ultrasound as preferred by an operator. In accordance with several different embodiments, the trocars 602 and 604 can be directed to the body tissues at various angles inclined with respect to the body of the patient.

Figure 10A:
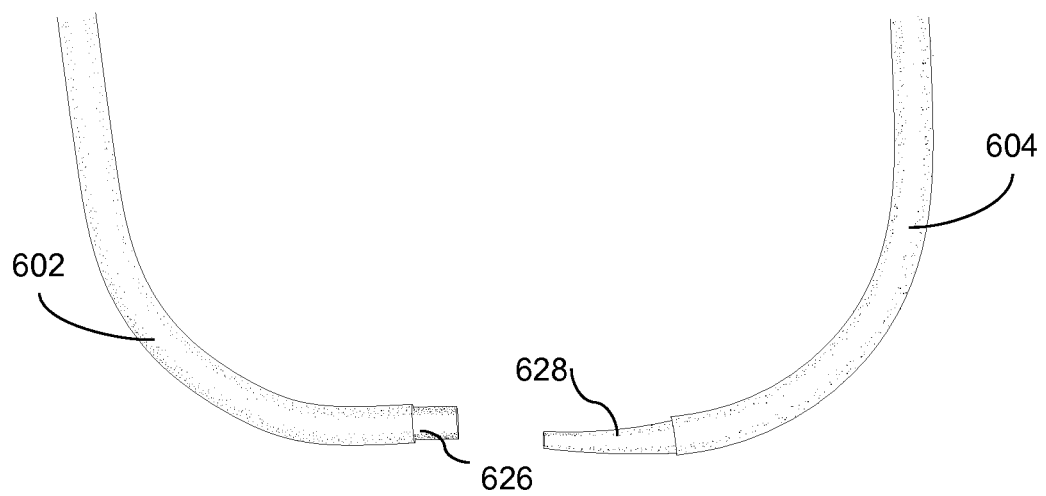
FIGS. 10A-10C illustrate different positions of the distal ends of the first trocar and the second trocar during mating or engagement, in accordance with an embodiment of the present invention.
Figure 10B:
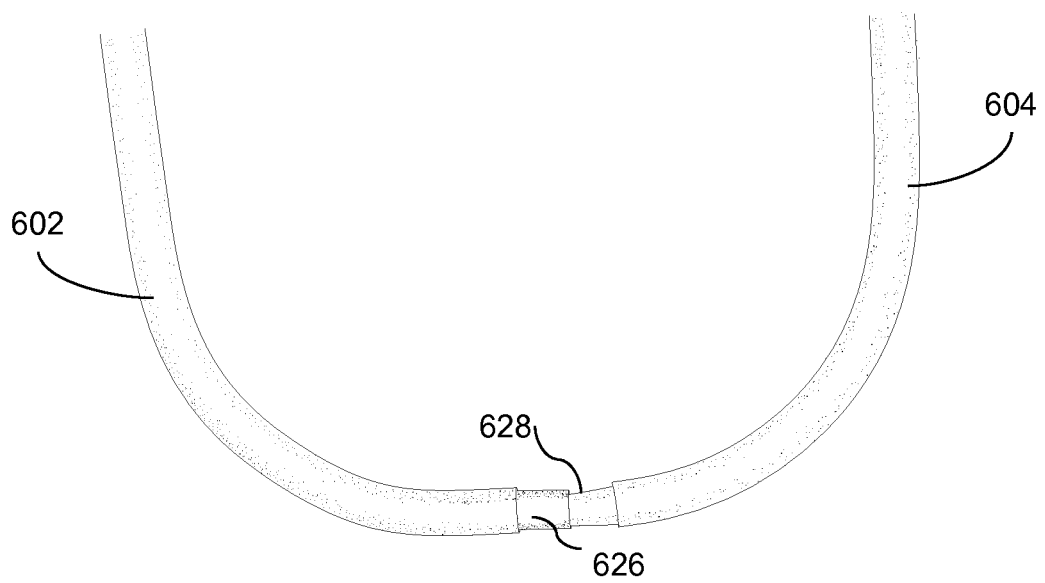
Figure 10C:
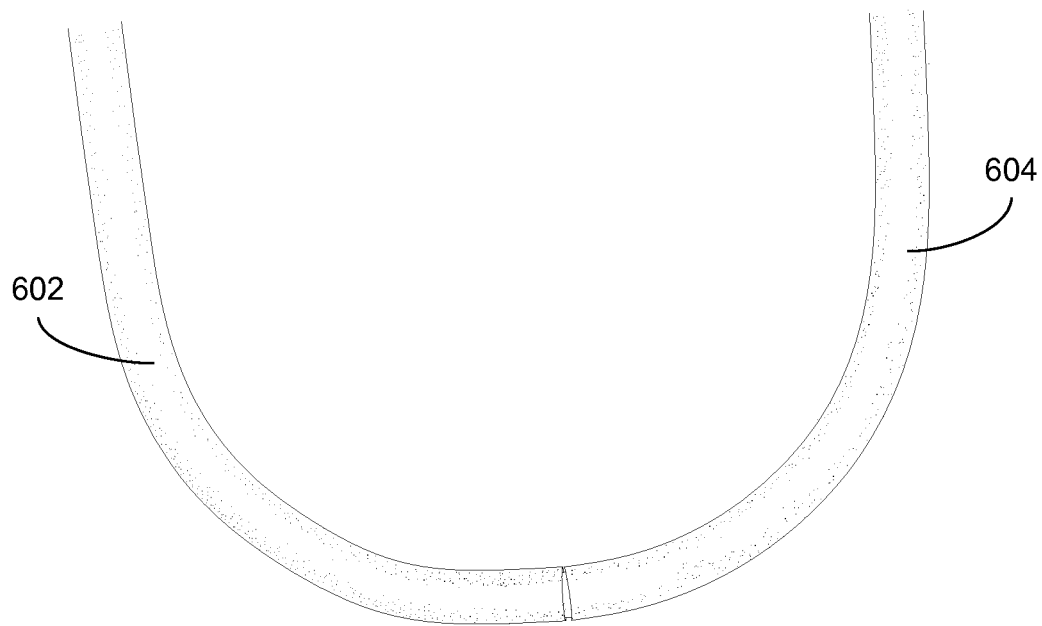

The first trocar 602 and the second trocar 604 are advanced to an extent that the distal end portion 626 of the first trocar 602 mates with the distal end portion 628 of the second trocar 604, at step 908. The distal end portions 626 and 628 of one or both the trocars 602 and 604 may be articulated in order to achieve distal mating of the trocars 602 and 604 inserted from any angle. The mating results in coupling of the engagement member 702 of the first trocar 602 with the engagement member 704 of the second trocar 604, thereby resulting in removal or displacement of body tissues between the distal end portion 626 of the first trocar 602 and the distal end portion 628 of the second trocar 604. A schematic perspective illustration of mating of the distal end portions 626 and 628 of the two trocars 602 and 604 has been shown in FIGS. 10A, 10B, and 10C. In this manner, a continuous pathway is formed around the anal canal (or periphery thereof) extending from the first bodily incision 802 to the second bodily incision 804. In some embodiments, the continuous pathway is in the form of a passage through the body tissues or a lumen created therein having a diameter equal to the diameter of the elongated members 614 and 616 of the trocars 602 and 604.

Figure 11:
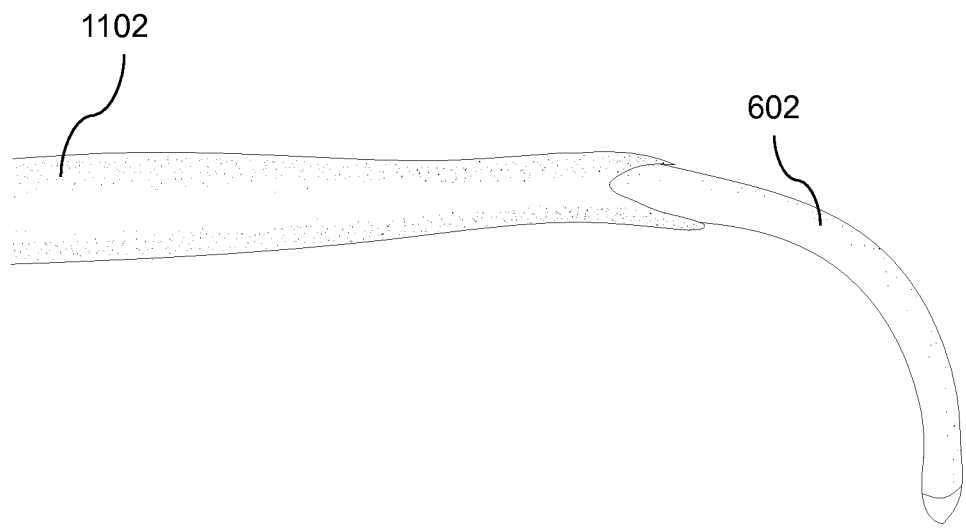
FIG. 11 illustrates a hollow tubular sheath disposed on a solid trocar for delivery of the bodily implant, in accordance various embodiments of the present invention.
Figure 12A:
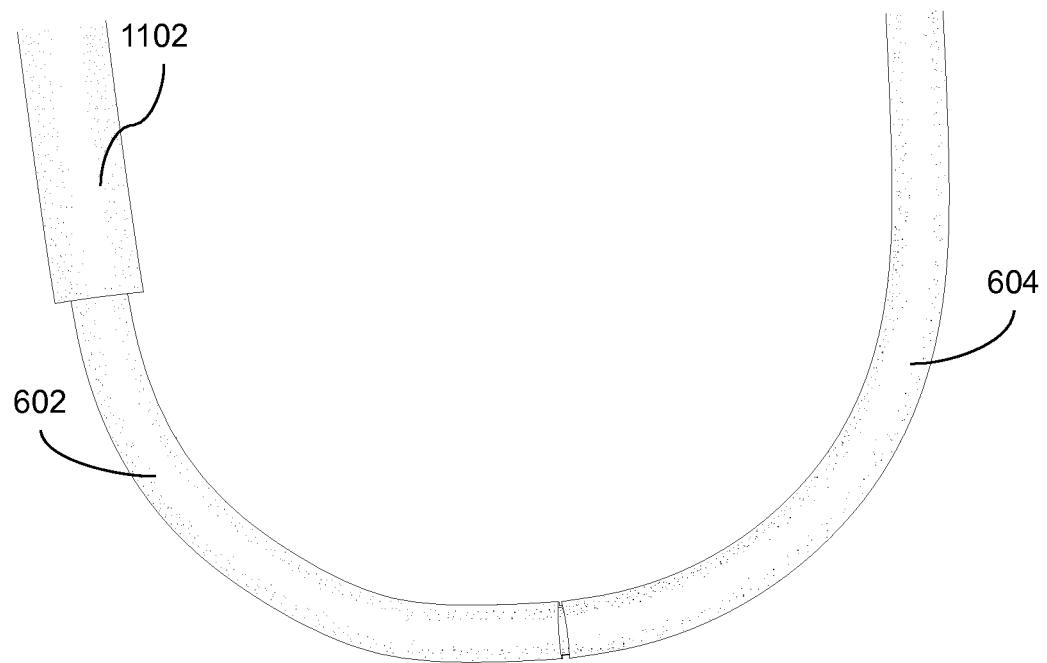
FIGS. 12A-12B illustrate a hollow tubular sheath disposed on a hollow trocar for delivery of the bodily implant, in accordance various embodiments of the present invention.
Figure 12B:
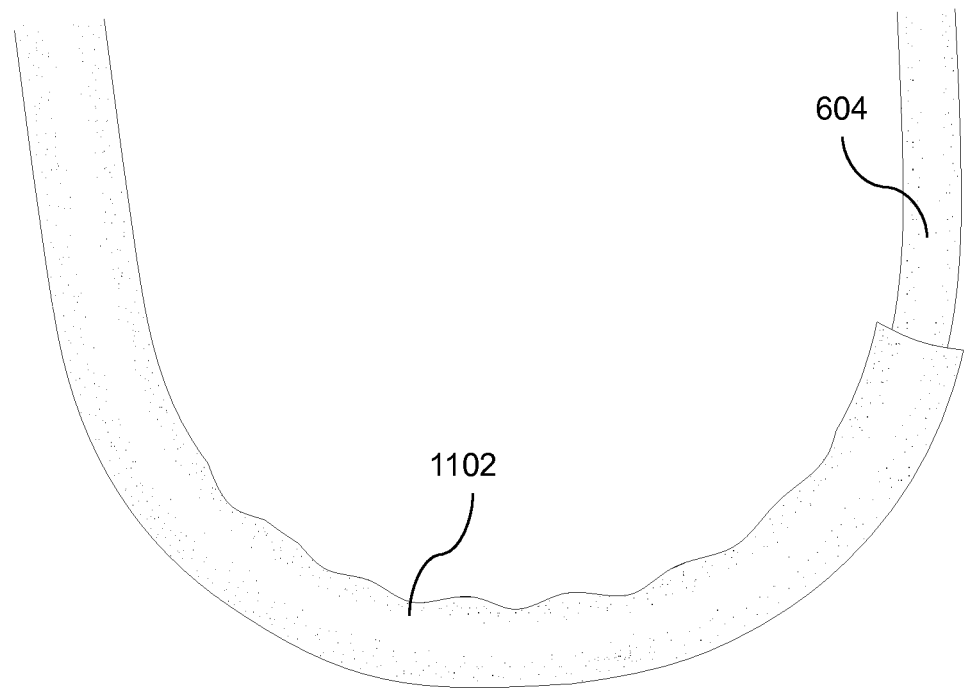

At step 910, a hollow tubular sheath 1102 (shown in FIG. 11 and FIGS. 12A and 12B) is disposed on the elongated members 614 and 616 of the first trocar 602 and the second trocar 604, respectively. In accordance with an embodiment, the hollow tubular sheath 1102 is disposed over the elongated members 614 and 616 of the trocars 602 and 604 such that the hollow tubular sheath 1102 covers an external periphery of the elongated members 614 and 616. This may be especially required if the trocars 602 and 604 are solid in nature as illustrated in FIG. 11. However, in another embodiment, the hollow tubular sheath 1102 can be disposed on the external periphery of the hollow trocars 602 and/or 604 also, as illustrated in FIGS. 12A and 12B. In accordance with still another embodiment of the present invention, the hollow tubular sheath 1102 is disposed inside the medical device 600. For example, the hollow tubular sheath 1102 may be inserted into a lumen defined by the medical device (i.e, the trocars). In accordance with several aspects of disposing the hollow tubular sheath 1102, a distal end of the hollow tubular sheath 1102 is positioned on the proximal end portion of the first trocar 602 from outside of the patient's body and subsequently introduced inside the body. The tubular sheath 1102 is introduced within the patient's body to an extent such that the distal end portion of the tubular sheath 1102 crosses over the two trocars 602 and 604, and finally comes out through the proximal end portion of the second trocar 604. Now, the two ends of the hollow tubular sheath 1102 stay outside the patient's body.

At step 912, the distal end portion 626 of the first trocar 602 is disengaged from the distal end portion 628 of the second trocar 604 such that the disengagement facilitates removal of the first trocar 602 and the second trocar 604 from the patient's body. In some embodiments, the disengagement of the distal end portion 626 of the first trocar 602 and the distal end portion 628 of the second trocar 604 may be obtained manually by articulating the distal end portions 626 and 628. In other embodiments, the disengagement may be obtained automatically by pressing a button provided on the handles 606 and 608 of the trocars 602 and 604. Thereafter, at step 914, the first trocar 602 and the second trocar 604 are removed from the patient's body leaving the hollow tubular sheath 1102 therein at its place. The hollow tubular sheath 1102 thus disposed acts as a cannula for delivery of the bodily implant 100 into the patient's body.

At step 916, the bodily implant 100 is delivered through the continuous pathway formed between the first bodily incision and the second bodily incision. The bodily implant 100 is delivered through a lumen defined by the hollow tubular sheath 1102. The operator such as a surgeon or a physician inserts a distal end of the bodily implant 100 into the patient's body from an end portion of the hollow tubular sheath 1102 that stays outside the body. The operator introduces the bodily implant 100 through the tubular sheath 1102 until it exits the patient's body from the other end of the tubular sheath 1102. In some embodiments, the operator may grasp a proximal end portion of the bodily implant 100 such that its advancement inside the body may be prevented while introducing the bodily implant 100 through the tubular sheath 1102.

Any known method may be used to introduce the bodily implant 100 into the tubular sheath 1102. For example, in some embodiments, the bodily implant 100 is introduced through the tubular sheath 1102 using a push type rod or other stiffening member. In other embodiments, a leader may be introduced through the tubular sheath 1102 and coupled to one end portion of the bodily implant 100. The bodily implant 100 may then be pulled into the tubular sheath 1102 using the leader.

Figure 19:
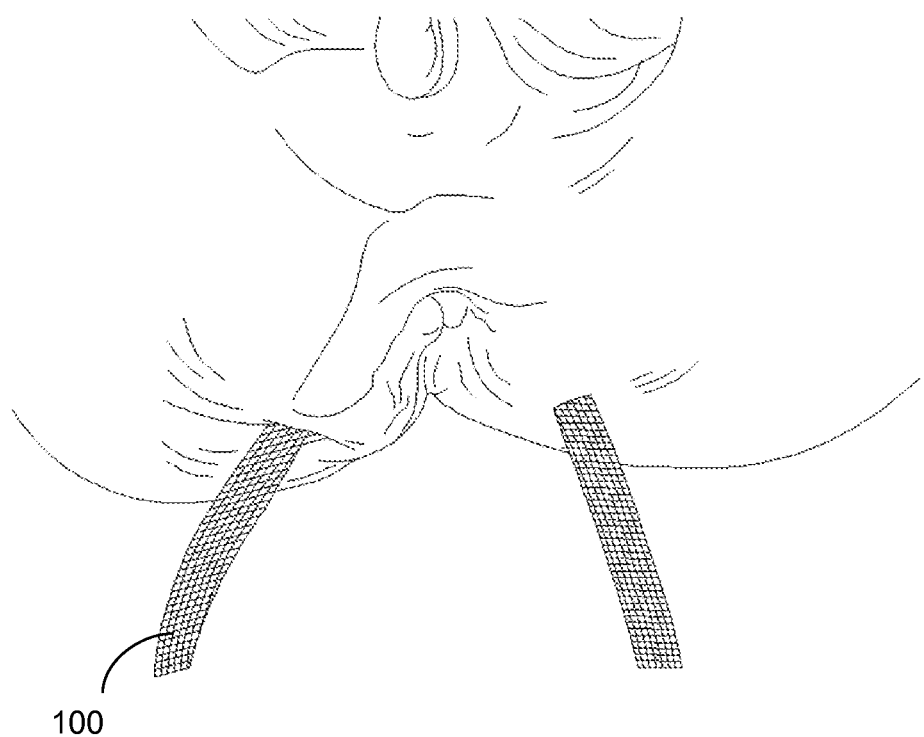
FIG. 19 illustrates a perspective view of a bodily implant disposed within a patient's body, in accordance with an embodiment of the present invention.

At step 918, the hollow tubular sheath 1102 is withdrawn from the patient's body, thereby leaving the bodily implant 100 at its place within the patient's body extending from the first bodily 802 incision, the second bodily incision 804, and around the anal canal. The bodily implant 100 is left to encircle the anal canal. The bodily implant 100 as disposed in the patient's body is shown in FIG. 19. The bodily implant 100 may be directed to encircle the anal canal only, or one or more ends of the bodily implant 100 may be passed through and/or be attached to other tissues or structures of the pelvis. In accordance with several different embodiments, the bodily implant 100 may be attached to appropriate tissues inside the patient's body such as within/through, and/or around, and/or between internal and/or external sphincters (subcutaneous, superficial, and/or deep); within/through perianal and/or postanal space; within conjoined longitudinal muscle; within/through anococccygeal body; within/through levator, gluteus maxims, transverse perianal, ischiocavernosus; within/through perianal body, obturator fossa and associated membranes and muscles; within/through ligaments such as uterosacral, cardinal, and/or round. Additionally, in some embodiments, the physician or person placing the bodily implant within a body of a patient may apply the correct tension to the bodily implant by pulling on the ends of the bodily implant.

In accordance with various embodiments, the ends of the implanted bodily implant may be tied or coupled to, for example sutures, staples, adhesives, pins, and the like with the body tissues. In some cases, the pressure from the body tissues may provide enough support for fixing the bodily implant within the body tissues. In some embodiments, free ends of the bodily implant that remain outside the incision can be trimmed away before closing the wound.

Figure 13A:
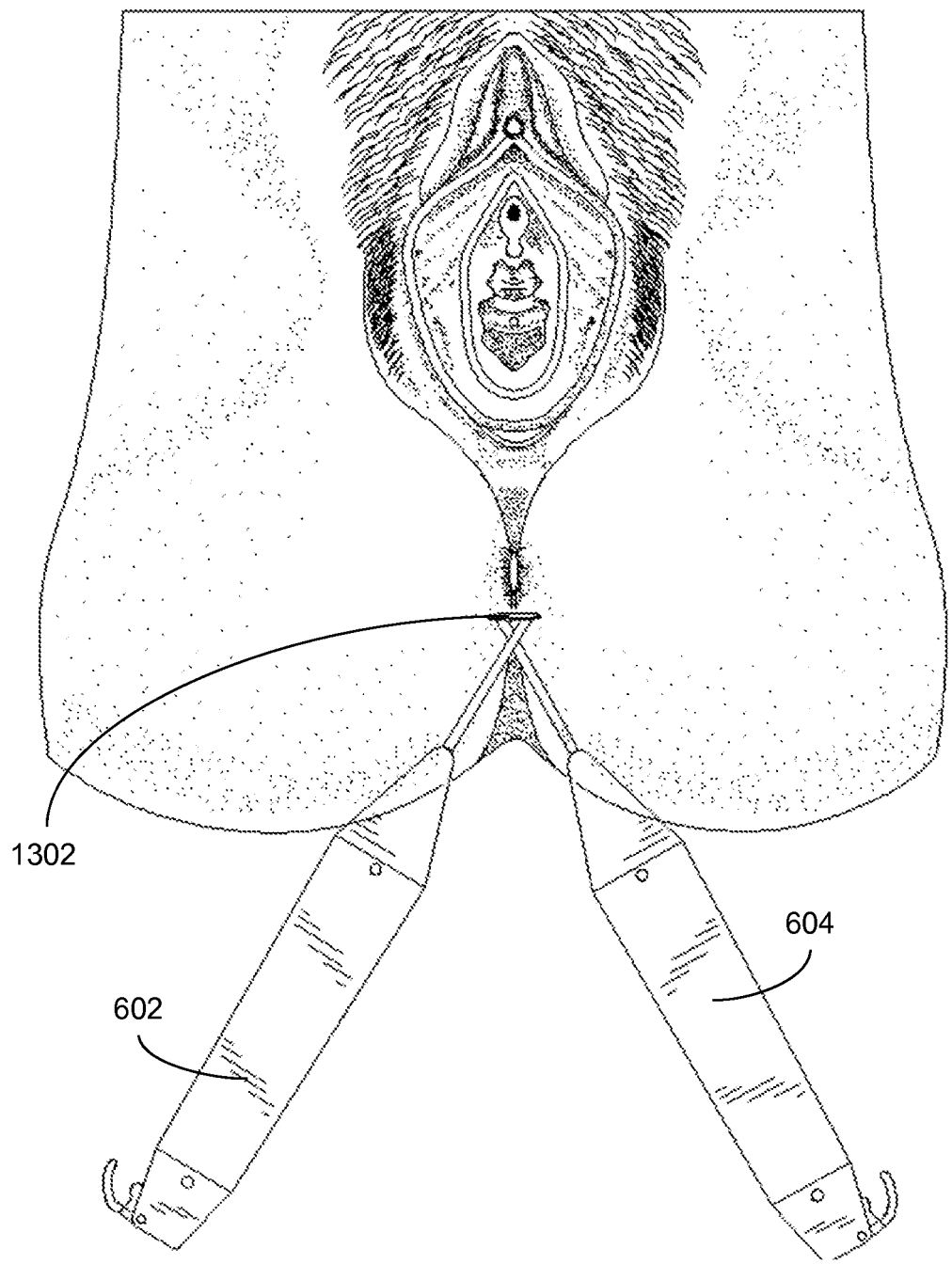
FIGS. 13A-13F illustrate a medical device delivering a bodily implant into a patient's body, in accordance with an embodiment of the present invention.
Figure 13B:
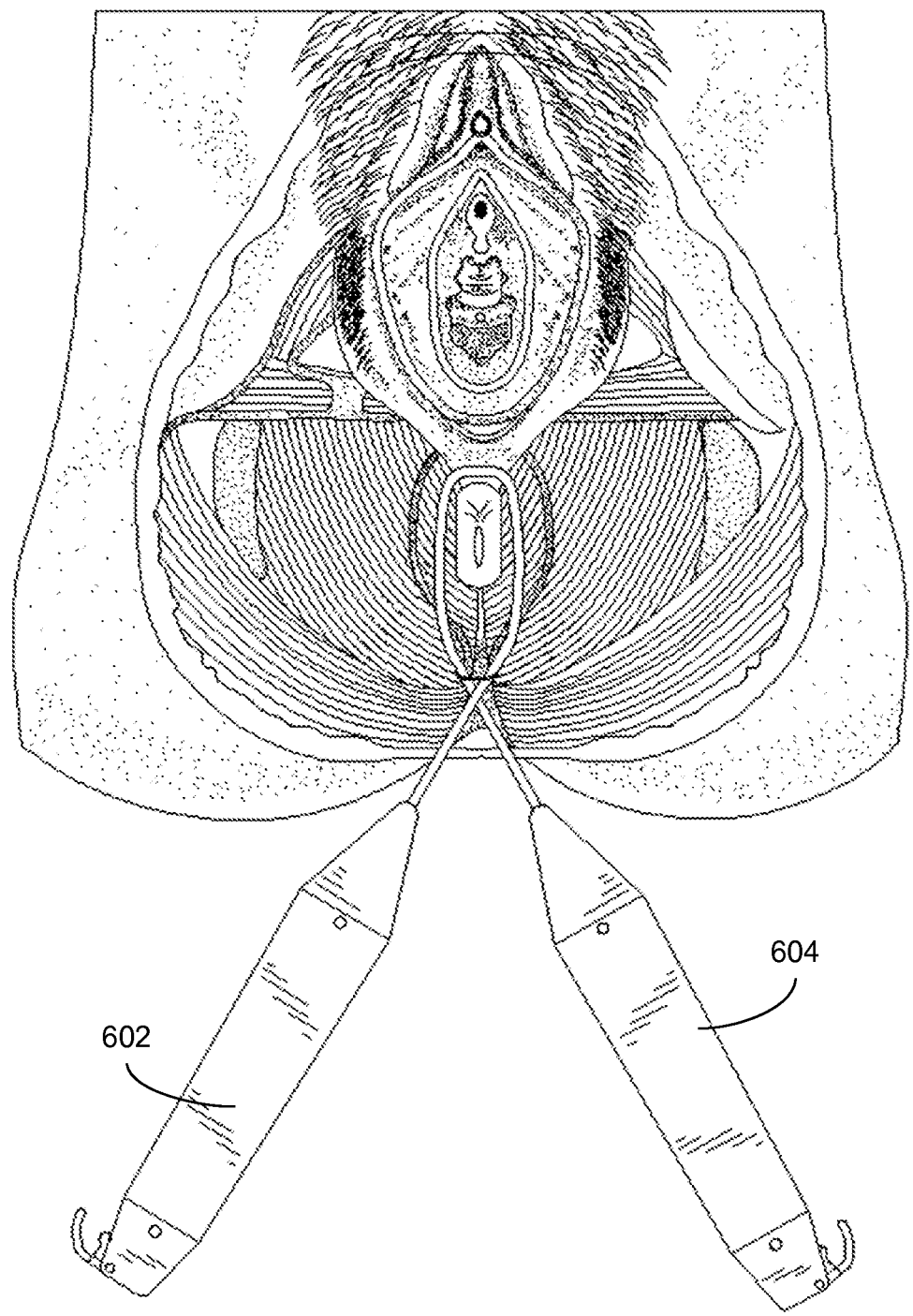
Figure 13C:
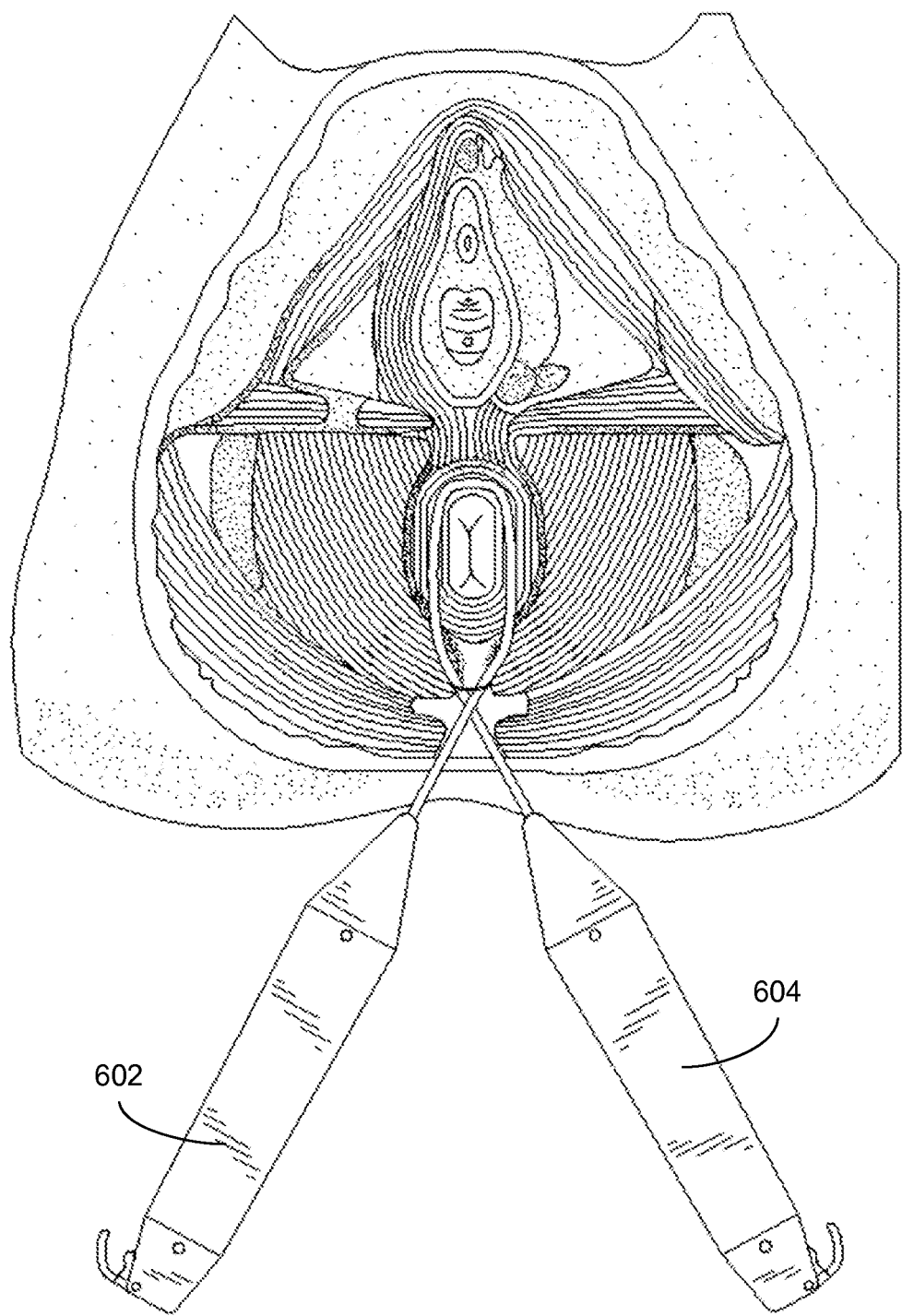
Figure 13D:
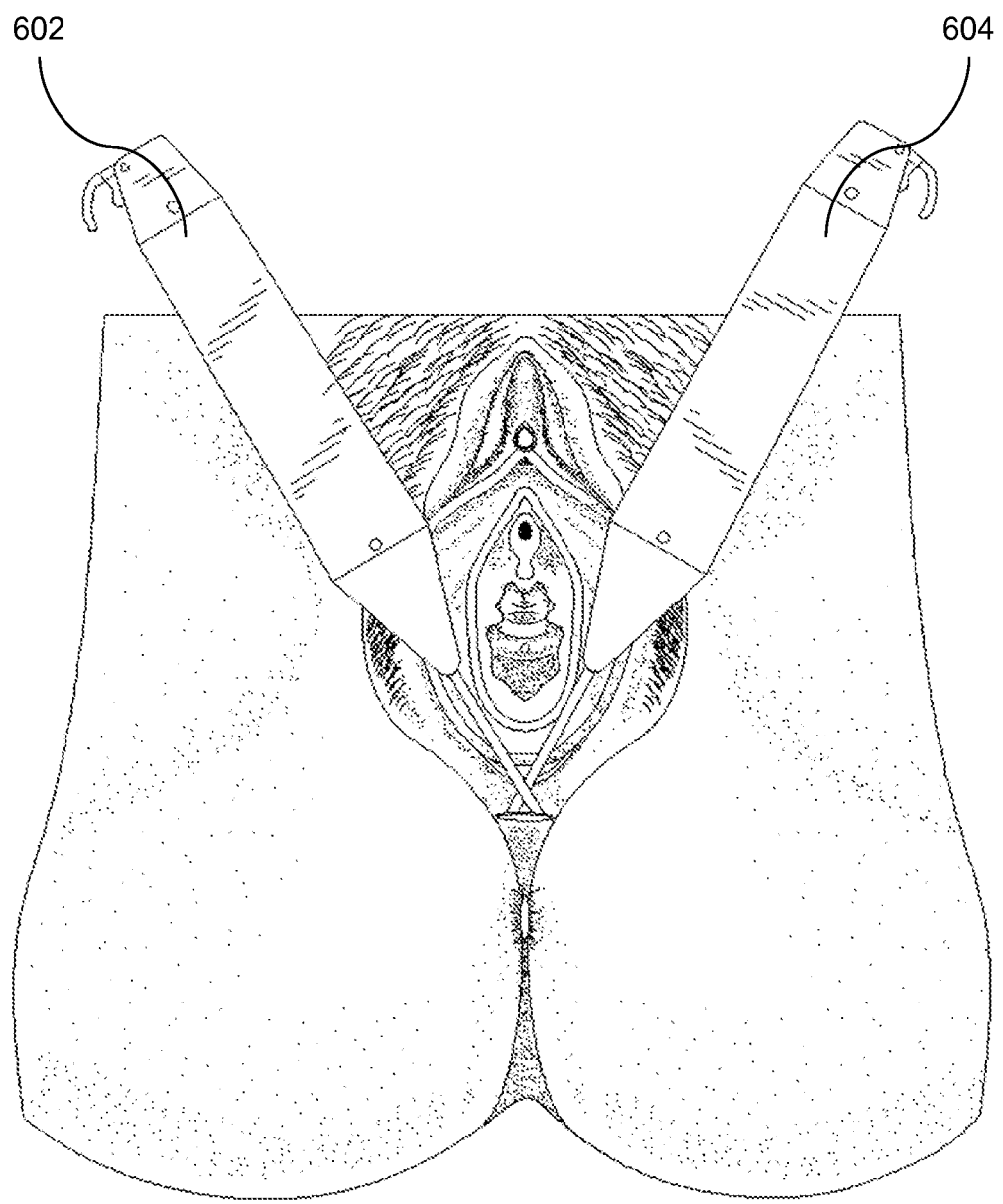
Figure 13E:
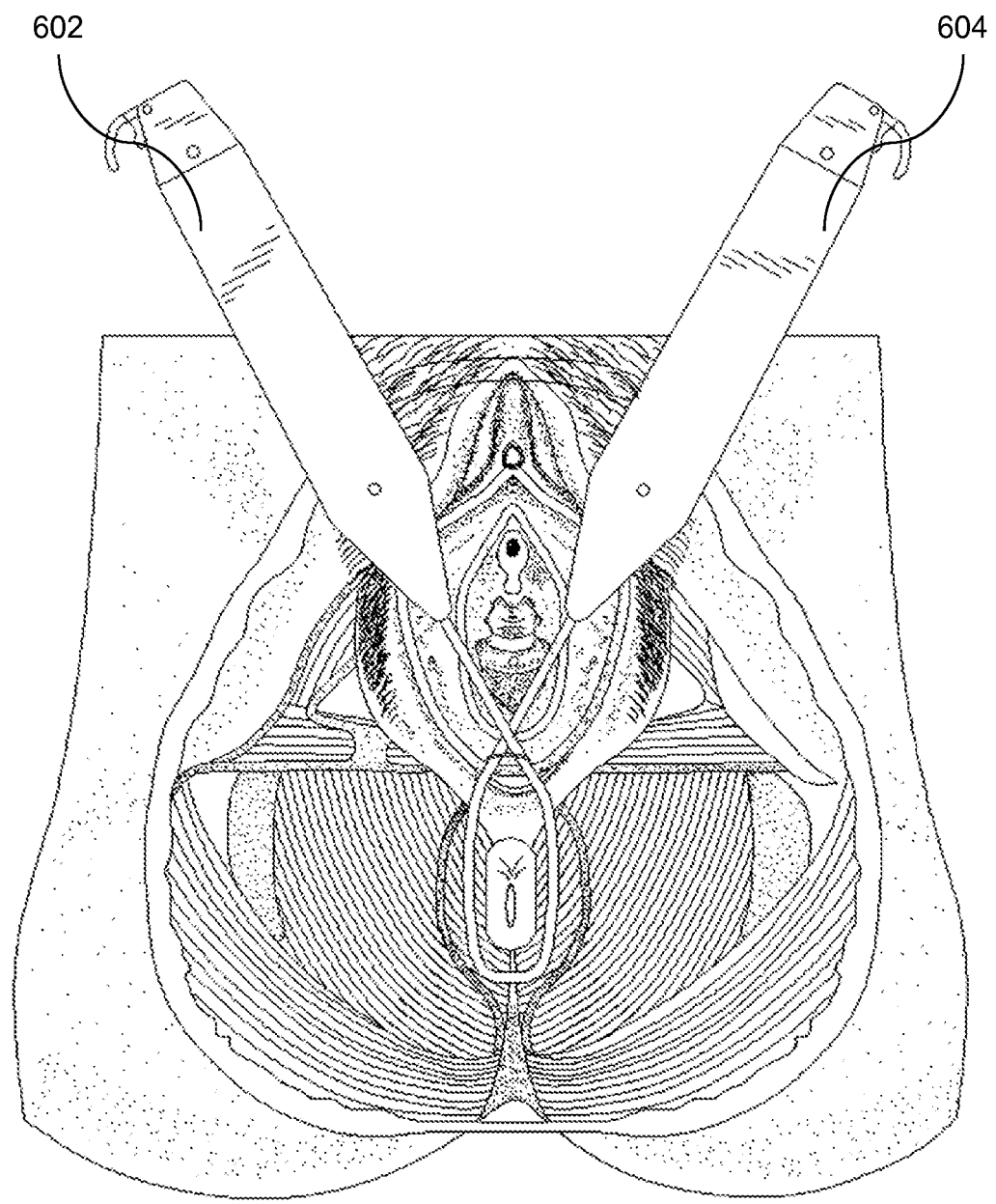
Figure 13F:
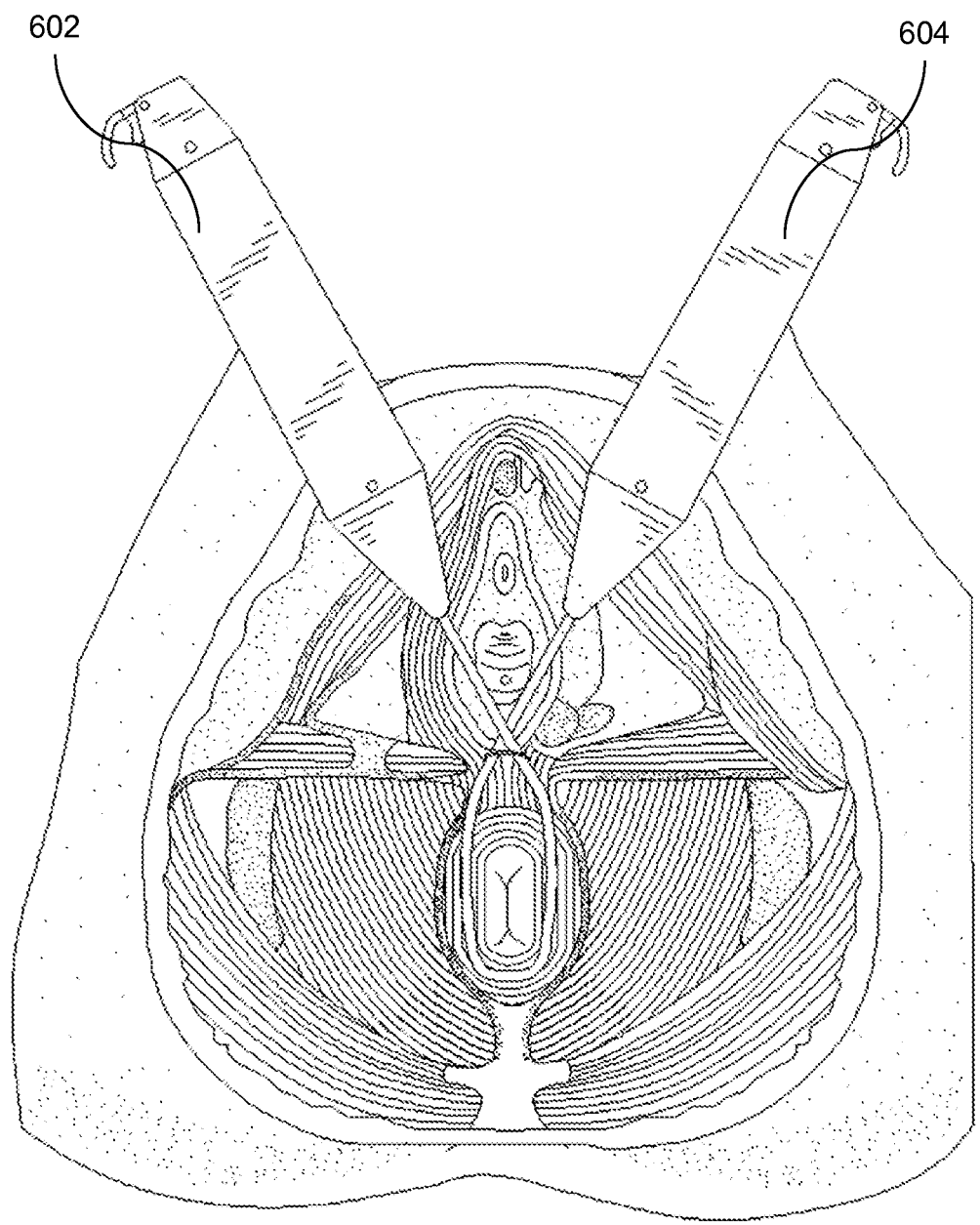

Referring to FIGS. 13A-13F, there is disclosed an illustration of the delivery of bodily implants such as the bodily implant 100 into the patient's body with the use of the medical device 600, in accordance with an embodiment of the present invention. The delivery and placement of the bodily implant 100 is shown in the female anatomical structure. As depicted, the bodily implant 100 is delivered and implanted around the anal canal with the use of a single incision. In a first aspect, the single incision is made in a middle posterior location to the anal canal as shown in FIGS. 13A, 13B, and 13C. As illustrated in FIGS. 13A, 13B, and 13C the two trocars 602 and 604 of the medical device 600 may be inserted through the skin incision, through the fat or other tissue layer, and into anal sphincter muscles or other tissue proximate to the anal canal in a substantially middle posterior location to the anus. In one embodiment, the single incision is made in the perennial body or perineum of the patient as shown in FIGS. 13D, 13E, and 13F. The two trocars 602 and 604 of the medical device 600 may be inserted through skin incisions, through the fat or other tissue layer, and into anal sphincter muscles or other tissues or tissues. The single incision described at the middle posterior and the perennial locations is merely for illustrative and exemplary purposes. And in a similar manner, the single incision may be made at various other locations such as lateral, posterolateral and anterolateral positions, and the like without limiting the spirit and the scope of the present invention.

Figure 14:
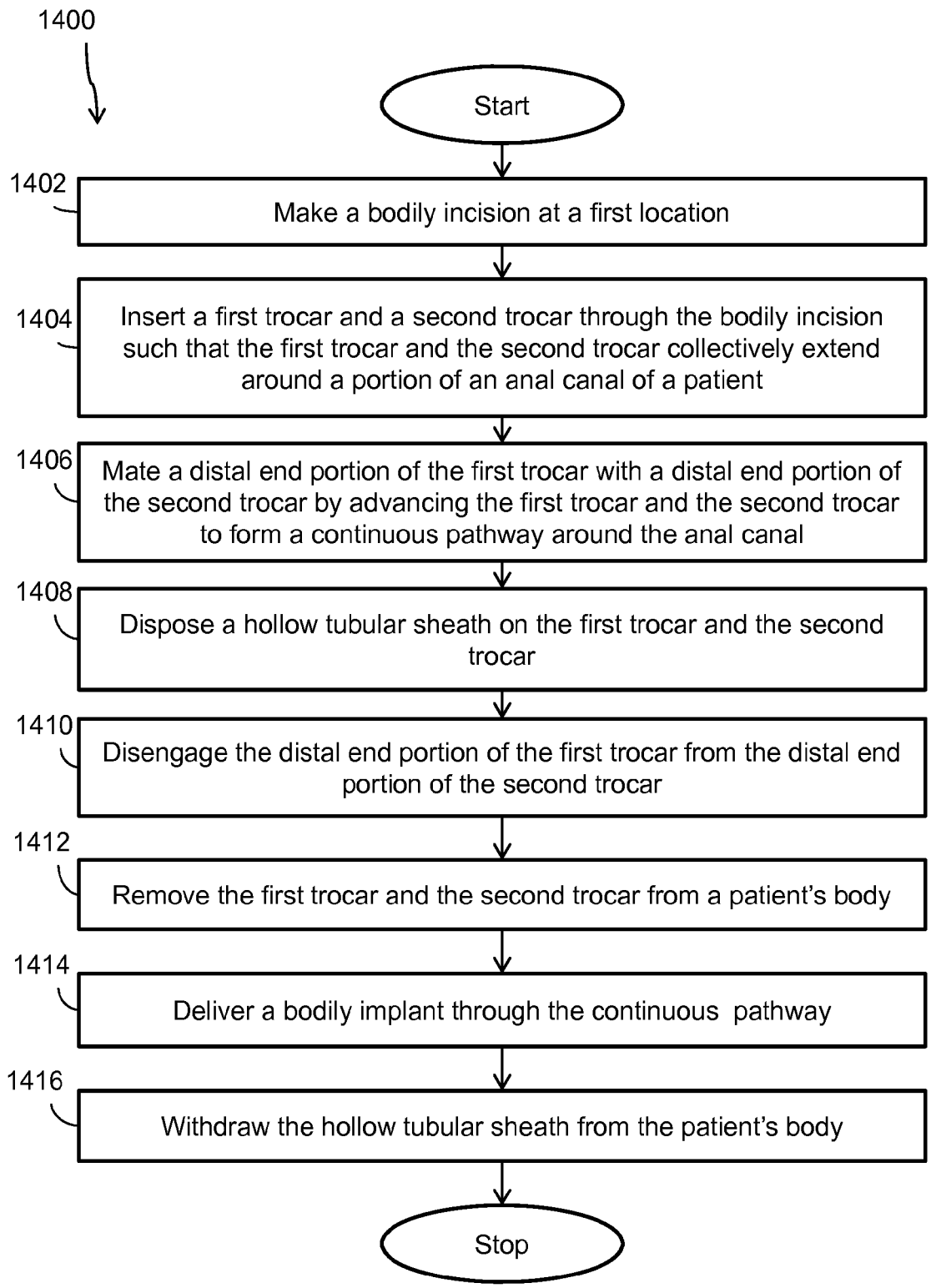
FIG. 14 is a flowchart illustrating a method of delivery and implant of the bodily implant, in accordance with an embodiment of the invention.

FIG. 14 is a flowchart illustrating a method 1400 of delivery and implantation of bodily implants such as the bodily implant 100, in accordance with an embodiment of the present invention. As illustrated in FIG. 14, the method 1400 includes making a single bodily incision at step 1402. In accordance with an embodiment as described in conjunction with FIGS. 13A-13C, the single bodily incision (hereafter referred to as bodily incision for simplicity of the description) is made at a substantially middle posterior location to the anus of the patient. In some embodiments, the bodily incision is made in the perineum of the patient. The middle posterior or the perennial incision can be made with the use of the medical device 600, or scalpel, as described in conjunction with FIG. 6 having two trocars 602 and 604, where any of the two trocars 602 and 604 may be used for making the bodily incision.

At step 1404, the first trocar 602 and the second trocar 604 are inserted in or through the bodily incision such that the first trocar 602 and the second trocar 604 collectively extend around a portion of an anal canal of a patient. In some embodiments, the first trocar 602 and the second trocar 604 are inserted in or through the bodily incision through a percutaneous passage around (either entirely around or partially around) the periphery or the tissue located proximate of the anal canal such that the first trocar 602 and the second trocar 604 collectively extend around a portion of an anal canal of a patient. The trocars 602 and 604 can be directed to proper body tissues or tissue planes by manual transanal or transcutaneous palpation and/or transanal ultrasound as preferred by the operator. During insertion, the distal end portion 626 of the first trocar 602 and the distal end portion 628 of the second trocar 604 face toward either side of the anal canal in a cross trocar manner. For example, if the distal end portion 626 of the first trocar 602 is inserted and advanced across the right side of the anal canal, the distal end portion 628 of the second trocar 604 is advanced across the left side of the anal canal from the same incision. The two trocars 602 and 604 are advanced to an extent that the distal end portion 626 of the first trocar 602 mates or engages with the distal end portion 628 of the second trocar 604 at step 1406 at a location substantially opposite to the incision beyond anus. The distal end portion of one or both trocars 602 and 604 may be articulated in order to achieve distal mating of the trocars 602 and 604 inserted from any angle. The mating or engagement results in coupling of the engagement member 702 of the first trocar 602 with the engagement member 704 of the second trocar 604, thereby resulting in removal or displacement of body tissues (i.e., a continuous pathway is formed) between the distal end portion 626 of the first trocar 602 and the distal end portion 628 of the second trocar 604. A schematic perspective illustration of mating of the distal end portions 626 and 628 of the two trocars 602 and 604 has been shown in FIGS. 10A, 10B, and 10C. In this manner, a continuous pathway is formed around the periphery of the anal canal such that the continuous pathway extends from the bodily incision and circumferentially ends at the same bodily incision. The continuous pathway is in the form of a passage through the body tissues or a lumen created therein having a diameter equal to the diameter of the elongated members 614 and 616 of the trocars 602 and 604.

At step 1408, the hollow tubular sheath 1102 is disposed on the elongated members 614 and 616 of the first trocar 602 and the second trocar 604 in a manner similar to that described in conjunction with FIG. 9.

At step 1410, the distal end portion 626 of the first trocar 602 is disengaged from the distal end portion 628 of the second trocar 604 such that the disengagement facilitates removal of the first trocar 602 and the second trocar 604 from the patient's body. Thereafter, at step 1412, the first trocar 602 and the second trocar 604 are removed from the patient's body leaving the hollow tubular sheath 1102 therein at its place. The hollow tubular sheath 1102 thus disposed acts as a cannula for delivery of the bodily implant 100 inside the patient's body.

At step 1414, the bodily implant 100 is delivered through the continuous pathway and through the lumen provided by the hollow tubular sheath 1102. This has been described in conjunction with FIG. 9 in detail.

At step 1416, the hollow tubular sheath 1102 is withdrawn from the patient's body, thereby leaving the bodily implant 100 at its place within the patient's body extending from the bodily incision, circumferentially surrounding the anal canal, and then coming out from the same bodily incision outside the patient's body. In accordance with several different embodiments, the bodily implant 100 may be attached to appropriate tissues inside the patient's body as has been described in conjunction with FIG. 9.

Figure 15:
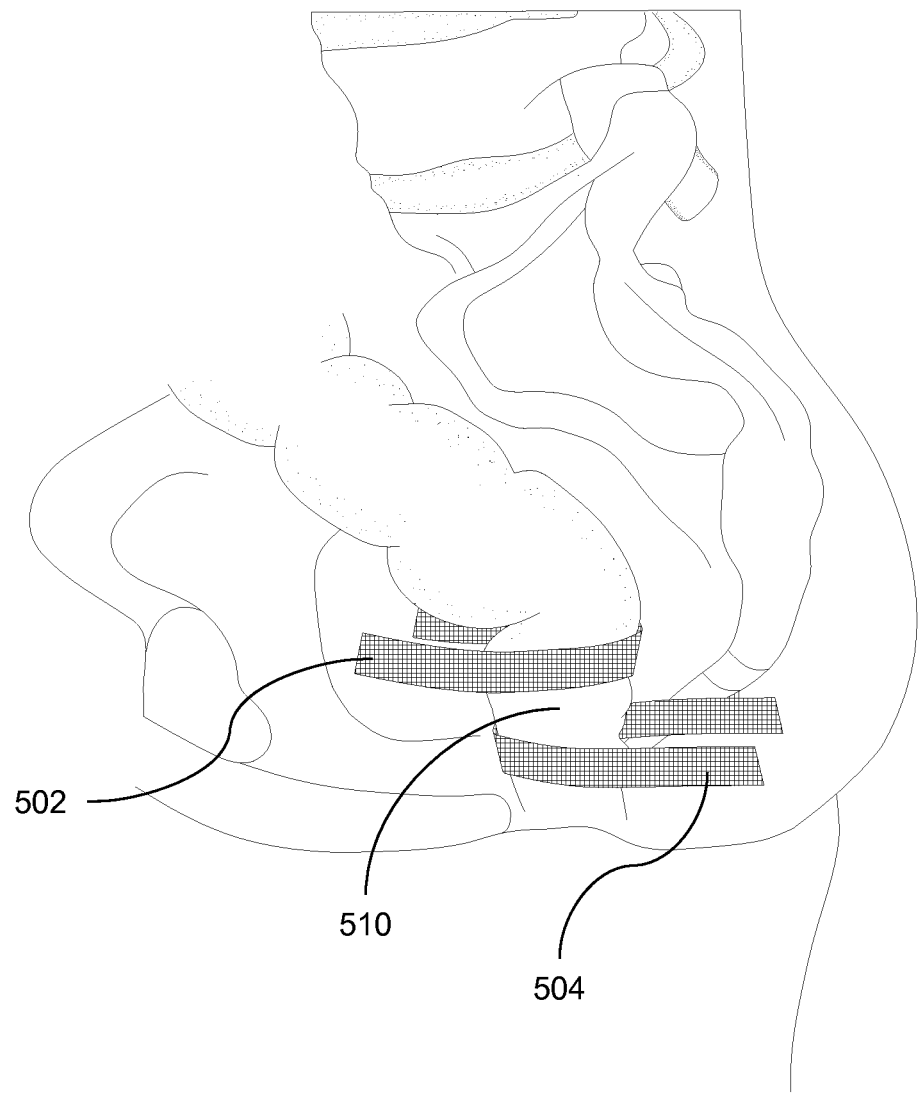
FIG. 15 illustrates a bodily implant delivered into a patient's body, in accordance with an embodiment of the present invention.

Referring to FIG. 15, there is disclosed an illustration of the delivery of the device 500 into the patient's body, in accordance with an embodiment of the present invention. The device 500, in accordance with this embodiment is described in conjunction with FIG. 3 in detail. As illustrated in FIG. 15, a first bodily implant (the first member 502) is positioned anteriorly to the anal canal 510 and a second bodily implant (the second member 504) is positioned posteriorly to the anal canal 510. The first member 502 and the second member 504 are longitudinally spaced from one another. In accordance with this embodiment, the first member 502 and the second member 504 are not placed directly at or close to an anus of a patient, but further up the anal canal 510 of the patient. In an exemplary scenario, the distance between the position of the first member 502 and the second member 504 can be three or four inches. The surgical procedure of delivery and placement of the device 500 in accordance with this embodiment is described herein.

Figure 16A:
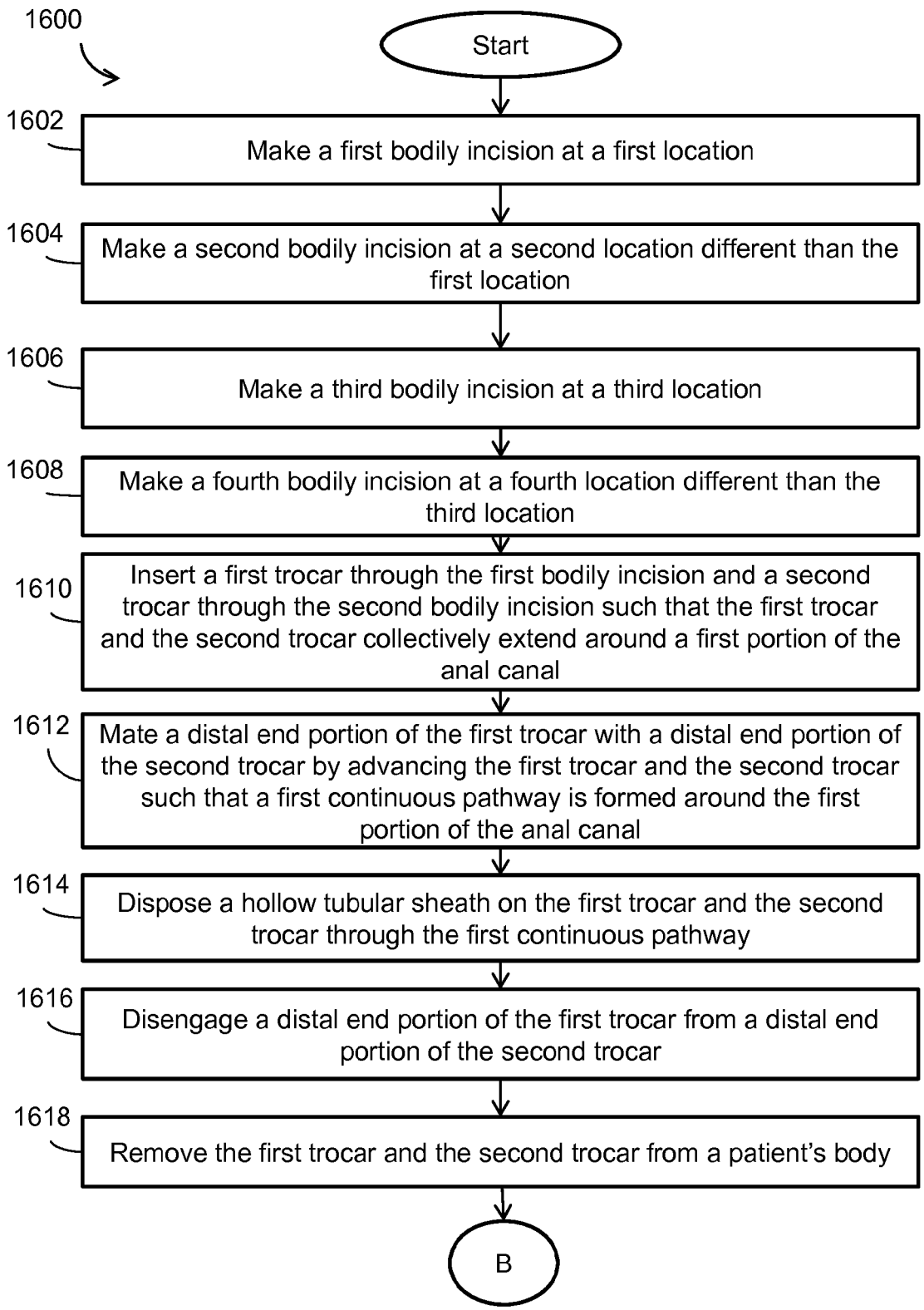
FIGS. 16A-16B represent a flowchart illustrating a method of delivery and implant of the bodily implant, in accordance with an embodiment of the invention.
Figure 16B:
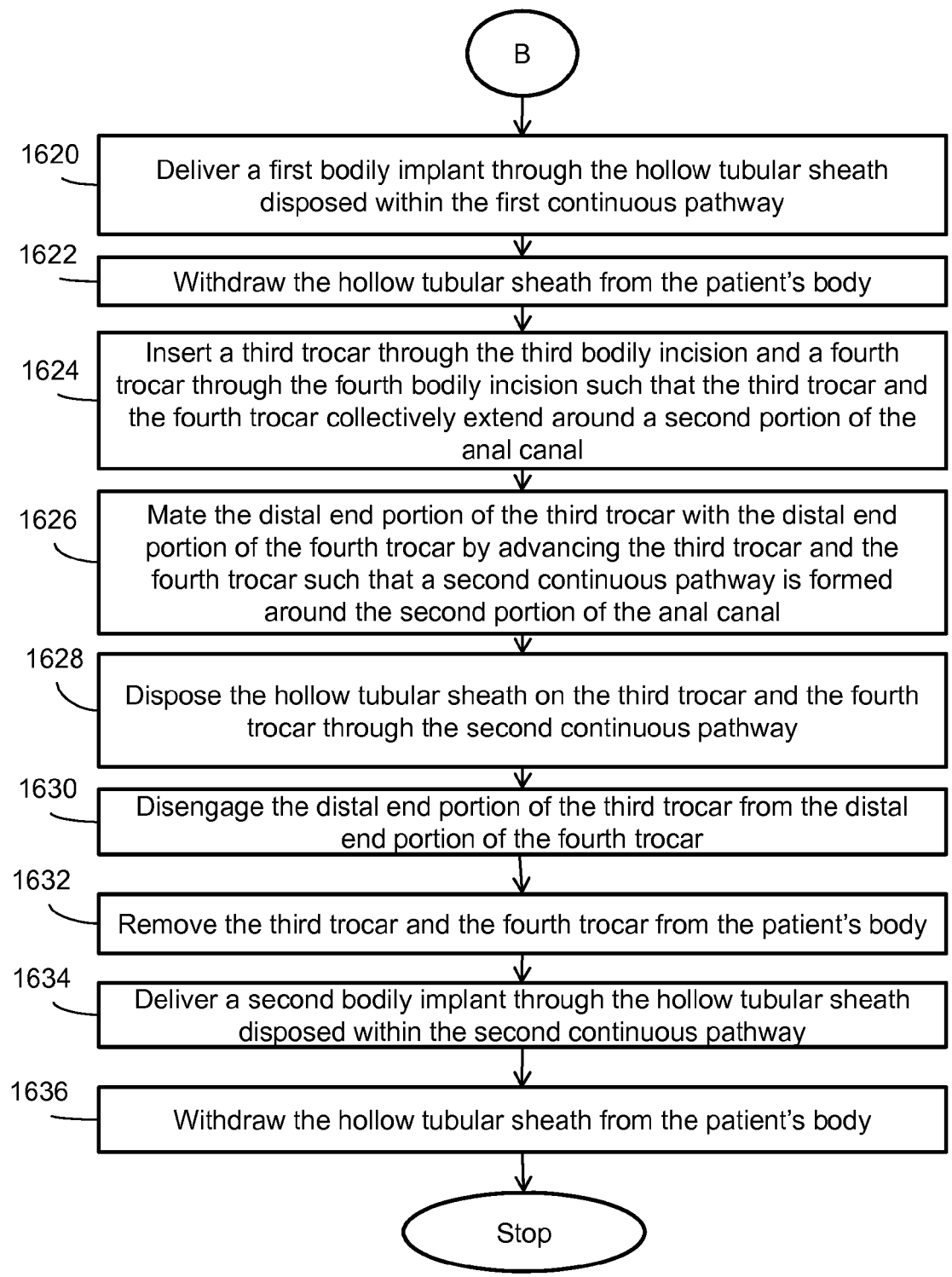

FIG. 16 is a flowchart illustrating a method 1600 of delivery and implant of the device 500, in accordance with an embodiment. As illustrated in FIG. 16, the method 1600 includes making a first bodily incision at a first location at step 1602 by the medical device 600 having the first trocar 602 and the second trocar 604. At step 1604, a second bodily incision is made at a second location by the medical device 600. The second location is different than the first location. The first and the second locations are substantially anterior to the anal canal of the patient.

At step 1606, a third bodily incision is made at a third location. At step 1608, a fourth bodily incision is made at a fourth location. The third location is different than the fourth location. The third and the fourth locations are substantially posterior to the anal canal of the patient.

At step 1610, the first trocar 602 is inserted through the first bodily incision and the second trocar 604 is inserted through the second bodily incision via a percutaneous passage around the periphery of the anal canal such that the first trocar and the second trocar collectively extend around a first portion of the anal canal. The first trocar 602 and the second trocar 604 are advanced to an extent that the distal end portion 626 of the first trocar 602 mates or engages with the distal end portion 628 of the second trocar 604 at step 1612. In this manner, a first continuous pathway is formed around the first portion of the anal canal. The first continuous pathway extends from the first bodily incision to the second bodily incision. The first continuous pathway is formed anteriorly to the anal canal.

At step 1614, the hollow tubular sheath 1102 is disposed on the elongated members 614 and 616 of the first trocar 602 and the second trocar 604 through the first continuous pathway. The procedure of disposing the hollow tubular sheath 1102 is similar to the manner described in conjunction with FIG. 9 in detail. Thereafter, at step 1616, the distal end portion 626 of the first trocar 602 is disengaged from the distal end portion 628 of the second trocar 604 such that the disengagement facilitates removal of the first trocar 602 and the second trocar 604 from the patient's body. Further, at step 1618, the first trocar 602 and the second trocar 604 are removed from the patient's body leaving the hollow tubular sheath 1102 therein at its place. The hollow tubular sheath 1102 thus disposed acts as the cannula for delivery of the first bodily implant (first member 502) inside the patient's body. The first member 502 has been described in conjunction with FIG. 5 in detail.

At step 1620, the first bodily implant (first member 502) is delivered through the lumen defined by the hollow tubular sheath 1102 disposed within the first continuous pathway. At step 1622, the hollow tubular sheath 1102 is withdrawn from the patient's body, thereby leaving the first member 502 at its place within the patient's body extending from the first bodily incision and the second bodily incision anteriorly to the anal canal. The first member 502 is left to encircle the anal canal.

At step 1624, a third trocar is inserted through the third bodily incision and a fourth trocar is inserted through the fourth bodily incision via a percutaneous passage around the periphery of the anal canal such that the third trocar and the fourth trocar collectively extend around a second portion of the anal canal. The third trocar and the fourth trocar are advanced to an extent that a distal end portion of the third trocar mates or engages with a distal end portion of the fourth trocar at step 1626. In this manner, a second continuous pathway is formed around a second portion of the anal canal. The second continuous pathway extends from the third bodily incision to the fourth bodily incision. The second continuous pathway is formed posteriorly to the anal canal.

At step 1628, the hollow tubular sheath 1102 is disposed on elongated members of the third trocar and the fourth trocar, respectively through the second continuous pathway. Thereafter, at step 1630, the distal end portion of the third trocar is disengaged from the distal end portion of the fourth trocar such that the disengagement facilitates removal of the third trocar and the fourth trocar from the patient's body. Further, at step 1632, the third trocar and the fourth trocar are removed from the patient's body leaving the hollow tubular sheath 1102 therein at its place. The hollow tubular sheath 1102 thus disposed acts as the cannula for delivery of a second bodily implant (second member 504) inside the patient's body. The second member 504 has been described in conjunction with FIG. 5 in detail.

At step 1634, the second bodily implant (second member 504) is delivered through the lumen defined by the hollow tubular sheath 1102 disposed within the second continuous pathway. At step 1636, the hollow tubular sheath 1102 is withdrawn from the patient's body, thereby leaving the second member 504 at its place within the patient's body extending from the third bodily incision and the fourth bodily incision posteriorly to the anal canal. The second member 504 is left to encircle the anal canal. The placement of the second member 504 is done in a manner such that the first member 502 and the second member 504 are separated longitudinally one above the other, thereby forming a noose structure.

Figure 17A:
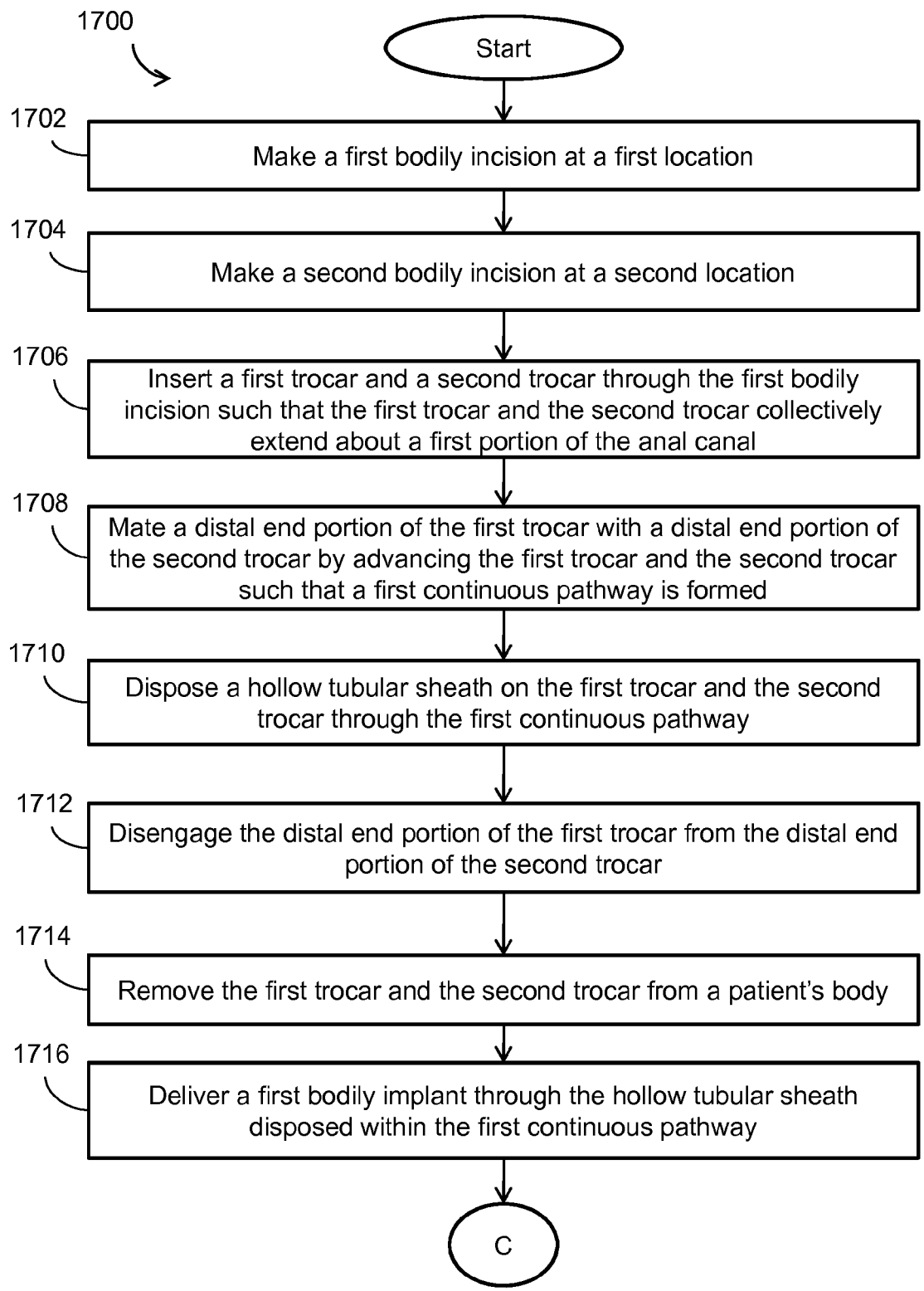
FIGS. 17A-17B is a flowchart illustrating a method of delivery and implant of a bodily implant, in accordance with an embodiment of the present invention.
Figure 17B:
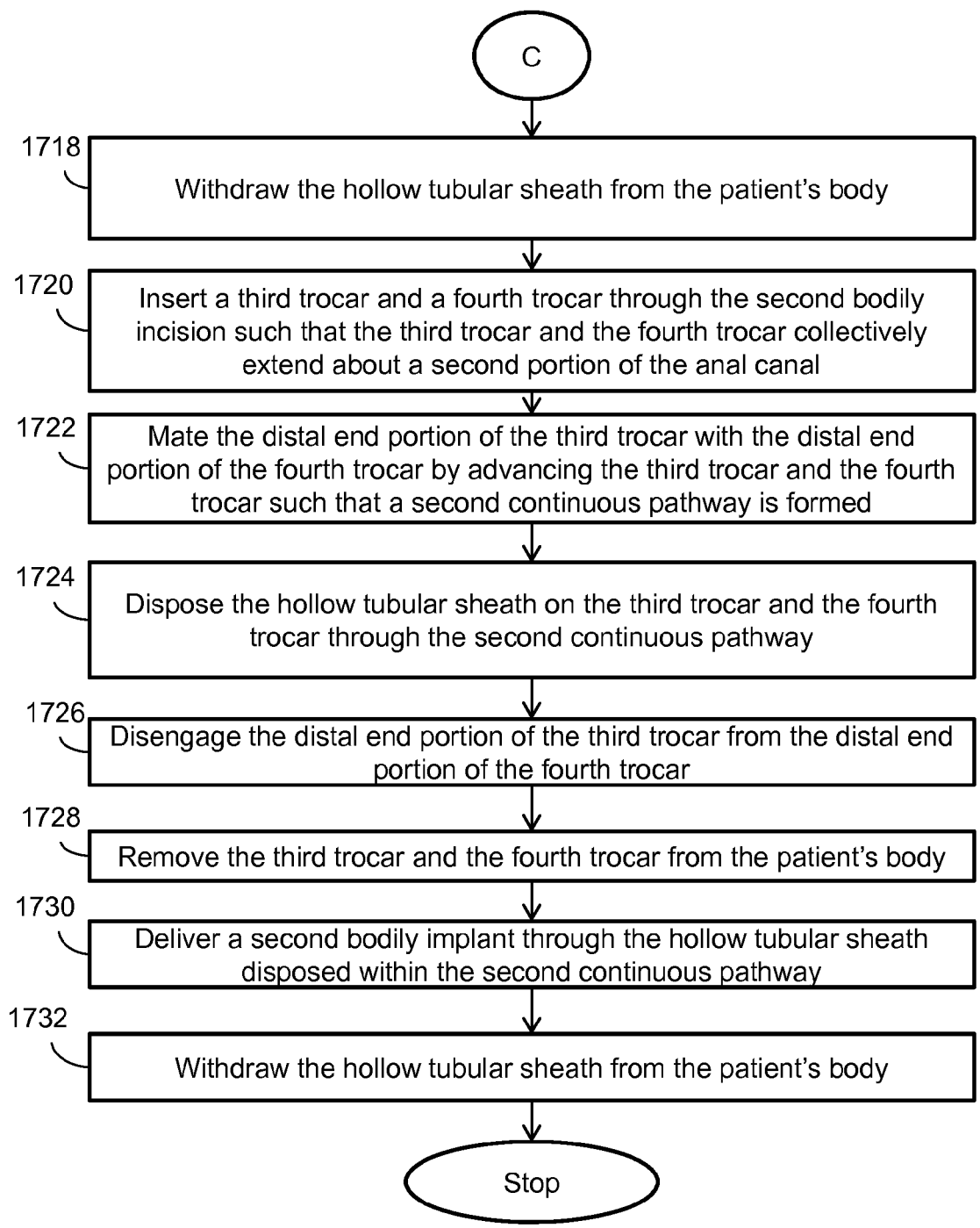

FIG. 17 is a flowchart illustrating a method 1700 of delivery and implant of the device 500, in accordance with an embodiment of the present invention. As illustrated in FIG. 17, the method 1700 includes making a first bodily incision at a first location at step 1702 by the medical device 600 having the first trocar 602 and the second trocar 604. The first location is substantially anterior to the anal canal of the patient. The medical device 600 has been described in conjunction with FIG. 6 in detail.

At step 1704, a second bodily incision is made at a second location by the medical device 600. The second location is substantially posterior to the anal canal of the patient.

At step 1706, the first trocar 602 and the second trocar 604 are inserted through the first bodily incision via a percutaneous passage around a periphery of the anal canal of the patient such that the first trocar and the second trocar collectively extend about a first portion of the anal canal. The first trocar 602 and the second trocar 604 are advanced to an extent that the distal end portion 626 of the first trocar 602 mates or engages with the distal end portion 628 of the second trocar 604, at step 1708. In this manner, a first continuous pathway is formed around the anal canal extending from the first bodily incision, circumferentially surrounding the anal canal, and coming out through the same first bodily incision.

At step 1710, the hollow tubular sheath 1102 is disposed on the elongated members 614 and 616 of the first trocar 602 and the second trocar 604, respectively through the first continuous pathway. The procedure of disposing the hollow tubular sheath 1102 is similar to the manner described in conjunction with FIG. 9 in detail.

Further, at step 1712, the distal end portion 626 of the first trocar 602 is disengaged from the distal end portion 628 of the second trocar 604 such that the disengagement facilitates removal of the first trocar 602 and the second trocar 604 from the patient's body. Thereafter, at step 1714, the first trocar 602 and the second trocar 604 are removed from the patient's body leaving the hollow tubular sheath 1102 therein at its place. The hollow tubular sheath 1102 thus disposed acts as the cannula for delivery of a first bodily implant (first member 502) inside the patient's body. The first member 502 has been described in conjunction with FIG. 5 in detail.

At step 1716, the first bodily implant (first member 502) is delivered through the lumen defined by the hollow tubular sheath 1102 disposed within the first continuous pathway. At step 1718, the hollow tubular sheath 1102 is withdrawn from the patient's body thereby leaving the first member 502 at its place within the patient's body extending from the first bodily incision, circumferentially surrounding the anal canal posteriorly, and coming out of the patient's body through the same first bodily incision. The first member 502 is left to encircle the anal canal.

At step 1720, a third trocar and a fourth trocar are inserted through the second bodily incision via a percutaneous passage around the periphery of the anal canal such that the third trocar and the fourth trocar collectively extend about a second portion of the anal canal. The third trocar and the fourth trocar are advanced to an extent that a distal end portion of the third trocar mates or engages with a distal end portion of the fourth trocar, at step 1722. In this manner, a second continuous pathway is formed around the periphery of the anal canal extending from the second bodily incision, circumferentially surrounding the anal canal posteriorly, and coming out of the patient's body through the same second bodily incision.

At step 1724, the hollow tubular sheath 1102 is disposed on the third trocar and the fourth trocar, respectively through the second continuous pathway. Thereafter, at step 1726, the distal end portion of the third trocar is disengaged from the distal end portion of the fourth trocar such that the disengagement facilitates removal of the third trocar and the fourth trocar from the patient's body. Further, at step 1728, the third trocar and the fourth trocar are removed from the patient's body leaving the hollow tubular sheath 1102 therein at its place. The hollow tubular sheath 1102 thus disposed acts as a cannula for the delivery of a second bodily implant (second member 504) inside the patient's body. The second member 504 has been described in conjunction with FIG. 5 in detail.

At step 1730, the second bodily implant (second member 504) is delivered through the lumen provided by the hollow tubular sheath 1102 disposed within the second continuous pathway. At step 1732, the hollow tubular sheath 1102 is withdrawn from the patient's body, thereby leaving the second member 504 at its place within the patient's body extending from the second bodily incision, circumferentially surrounding the anal canal posteriorly, and coming out of the patient's body through the same second bodily incision. The second member 504 is left to encircle the anal canal. The placement of the second member 504 is done in a manner such that the first member 502 and the second member 504 are separated longitudinally one above the other, thereby forming a noose structure.

The use of the hollow tubular sheath 1102 is described in conjunction with various embodiments described above to deliver the bodily implants such as the bodily implant 100. However, in certain other scenarios, the bodily implant 100 may be directly delivered through the lumen of the medical device 600 (hollow trocars) such that the tubular sheath 1102 is not required.

Figure 18:
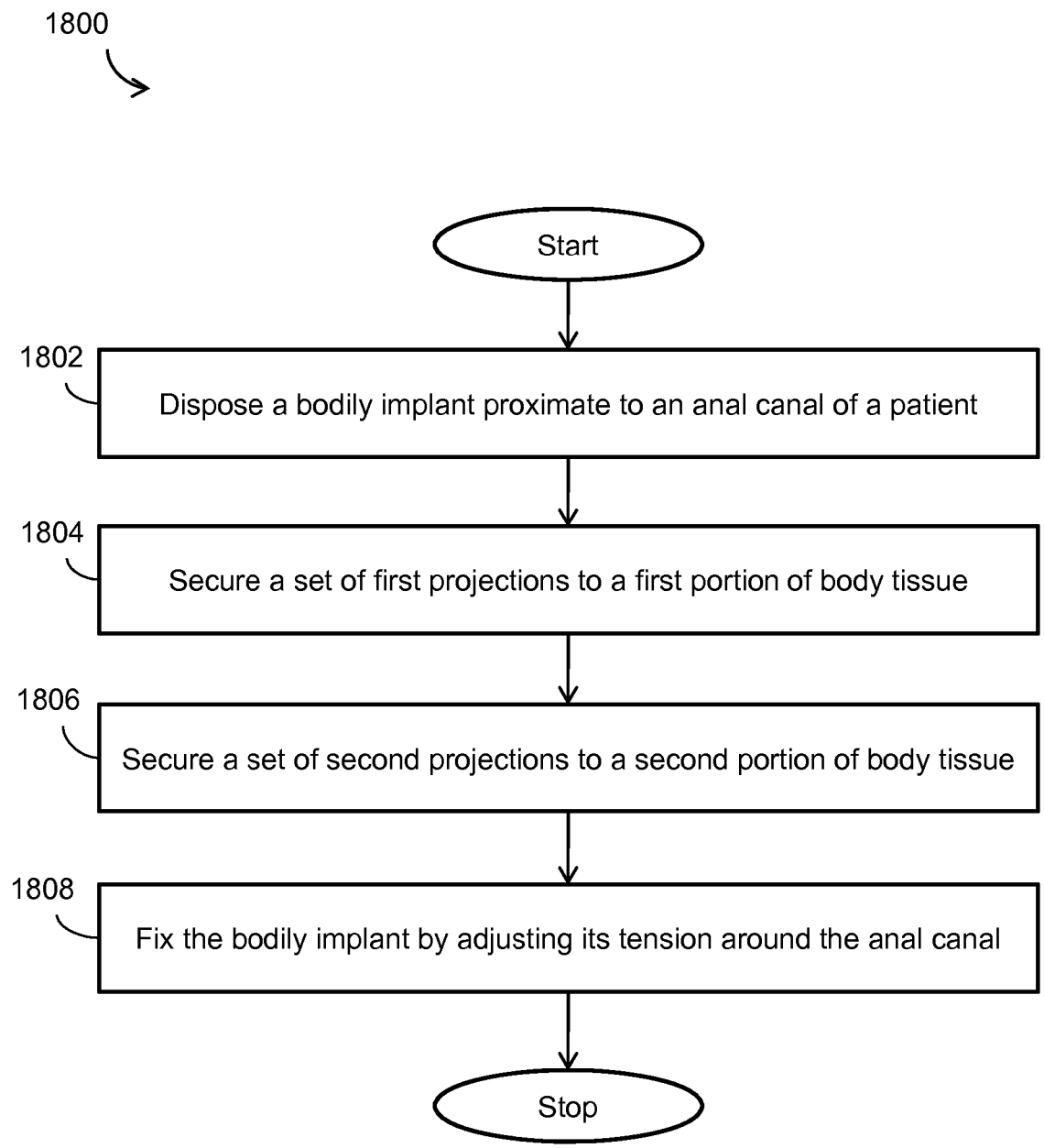
FIG. 18 is a flowchart illustrating a method of securing and fixing a bodily implant with body tissues, in accordance with an embodiment of the present invention.

FIG. 18 is a flowchart illustrating a method 1800 of securing and fixing bodily implants such as the bodily implant 100 with body tissues, in accordance with various embodiments of the present invention. The method 1800 includes disposing the bodily implant 100 proximate to an anal canal of the patient, at step 1802. The bodily implant 100 has been described in conjunction with FIGS. 1 in detail. The bodily implant 100 can be disposed using the medical device 600 as described in conjunction with FIG. 6. The procedure of disposing the bodily implant 100 in this case can be similar to the procedure of disposing the bodily implants in accordance with the embodiments described above. In other words, although the method is described with respect to bodily implant 100, any of the other above described bodily implants may be inserted into the body of the patient as described below. The bodily implant 100 may surround a complete or a portion of a periphery around the anal canal. In accordance with an aspect using the bodily implant 300 having a projectionless portion 302, the projectionless portion 302 may be fixed on a tear or a damage, such that the projectionless portion 302 may partially or wholly cover the tear or the damage. In another aspect of using the bodily implant 100, the tear or the damage may be covered by the set of the first projections 104 or the set of the second projections 106. The set of the first projections 104 and the set of the second projections 106 have been described earlier in conjunction with FIGS. 1-4 in detail.

At step 1804, the set of the first projections such as the set of the first projections 104 is secured to a first portion of body tissues. In this scenario, the set of the first projections 104 engages body tissues on a first side of the tear. The set of the first projections 104 allows movement of the bodily implant 100 with respect to the first portion of body tissue in a first direction and restricts the movement of the bodily implant 100 with respect to the first portion of body tissue in a second direction because of the inherent design of the projections.

At step 1806, the set of the second projections such as the set of the second projections 106 is secured to a second portion of the body tissues. In this scenario, the set of the second projections 106 engages a second portion of the body tissues on a second side of the tear. The set of the second projections 106 allows movement of the bodily implant 100 with respect to the second portion of body tissue in the second direction and restricts the movement of the bodily implant 100 with respect to the second portion of body tissue in the first direction because of the inherent design of the projections. The first portion of body tissue is disposed on the first side of the tear in bodily tissue and the second portion of body tissue is disposed on the second side of the tear in bodily tissue. In accordance with various embodiments, the tear may be a damage, a cut tissue, or any other unwanted effect around an anus, anal canal, rectum, anal sphincters, and the like of the patient.

At step 1808, the bodily implant 100 is fixed by adjusting its tension around the anal canal. Additionally, tissue portions that are coupled to the different sets of projections may be approximated by pulling on or applying tension to the different end portions of the bodily implant 100. The fixing of the bodily implant 100 is done by pulling one or both ends of the bodily implant 100. The pulling from a left end of the bodily implant 100 causes the set of the second projections 106 to engage the second portion of the body tissues and pull them toward the first side while the set of the first projections 104 disengages from the first portion of the body tissues. Similarly, the pulling from a right end of the bodily implant 100 causes the set of the first projections 104 to engage the first portion of the body tissues and pull them toward the second side while the set of the second projections 106 disengages from the second portion of the body tissues. In some embodiments, a bi-poling effect is generated in two directions. The pulling of the one or both ends of the bodily implant 100 pulls the body tissues close together such that a left end portion of the tear overlaps, joins, or moves closer to a right side of the tear. Thus, the tear is closed without even or traditional suturing or stitching of the two end portions of the tear.

In accordance with various embodiments, re-positioning of the bodily implant 100 may be done in case the bodily implant 100 is found to be placed incorrectly. In such a scenario, a hollow tubular member (not shown) may be inserted across a pathway created during delivery of the bodily implant 100 with the use of a trocar such as the trocar 602 or the trocar 604. During insertion, distal edges of the hollow tubular member provide a push force on the implanted bodily implant 100. This causes the set of the first projections 104 and/or the set of the second projections 106 to flatten and separate from the body tissues. The positioning of the bodily implant 100 may then be adjusted. Finally, the hollow tubular member may be removed from the patient's body to re-engage the projections 104 and 106 with bodily tissue to fix or retain the bodily implant 100 in place within the body of the patient. In an aspect, the hollow tubular sheath 1102 described in conjunction with FIG. 11 may also serve the purpose of the hollow tubular member.

The procedure of securing, fixing, and repositioning bodily implants has been described above in conjunction with the bodily implant 100. However, other bodily implants such as the bodily implant 200, the bodily implant 300, the bodily implant 400, and the bodily implant 500 may also be employed.

In accordance with various embodiments described above, use of two trocars is recommended to perform the surgeries. However, a single trocar may also be used to perform the surgical procedures without limiting the spirit and scope of the present invention.

The present invention has been described in conjunction with the bodily implant as illustrated in FIGS. 1-4. However, other kinds of bodily implants (including conventional devices), slings, support members, suture bundles, pull rods, sleeves, other bolstering materials, and the like may be equally used to be delivered into the patient's body with the use of the teachings of the invention.

In one general aspect, a method for the treatment of fecal incontinence can include disposing a bodily implant proximate to an anal canal of a patient where the bodily implant having a strip extending along a length between a first end portion and a second end portion, the strip having a set of first projections and a set of second projections extending along at least a portion of a longitudinal edge of the strip. The set of the first projections can be inclined toward the second end portion of the strip and the set of the second projections can be inclined toward the first end portion of the strip. The method can include securing the set of first projections to a first portion of body tissue such that the set of the first projections allows movement of the bodily implant with respect to the first portion of the body tissue in a first direction and restricts movement of the bodily implant with respect to the first portion of the body tissue in a second direction. The method can also include securing the set of the second projections to a second portion of the body tissue such that the set of the second projections allows movement of the bodily implant with respect to the second portion of the body tissue in the second direction and restricts movement of the bodily implant with respect to the second portion of the body tissue in the first direction.

In some embodiments, the first portion of the body tissue is disposed on a first side of a tear in bodily tissue and the second portion of the body tissue is disposed on a second side of the tear in bodily tissue. In some embodiments, the method can also include pulling the first end of the strip to adjust the position of the bodily implant within the body of the patient. In some embodiments, the method can also include re-positioning the bodily implant if the bodily implant is secured incorrectly. In some embodiments, the method can also include disposing a hollow tubular sheath over the bodily implant while the bodily implant is disposed within the body tissues such that the hollow tubular sheath disengages the first set of projections and/or the second set of projections from the body tissues to allow repositioning of the bodily implant within the body of the patient.

In another general aspect, a method for the treatment of fecal incontinence can also include making a first bodily incision at a first location and making a second bodily incision. The method can include inserting a first trocar through the first bodily incision and a second trocar through the second bodily incision such that the first trocar and second trocar collectively extend around an anal canal of a patient and such that a continuous pathway is formed between the first bodily incision and the second bodily incision. The method can also include delivering a bodily implant through the continuous pathway formed between the first bodily incision and the second bodily incision.

In some embodiments, the bodily implant is a mesh-based sling. In some embodiments, the bodily implant is a single fiber. In some embodiments, the bodily implant is a bundle of fibers. In some embodiments, the making of the first bodily incision can include making an incision at a location posteriolateral of the anal canal or at a location anteriolateral of the anal canal of the patient.

In some embodiments, the method can include mating a distal end portion of the first trocar with a distal end portion of the second trocar. In some embodiments, the method can include disposing a hollow tubular sheath over the first trocar and the second trocar. In some embodiments, the method can include removing the first trocar and the second trocar after the disposing the hollow tubular sheath. In some embodiments, the method can include disposing a hollow tubular sheath within lumens defined by the first trocar and the second trocar.

In some embodiments, the method can include removing the first trocar and the second trocar after the disposing the hollow tubular sheath. In some embodiments, the method can include disposing a solid tube in the hollow lumen of the first trocar and the second trocar. In some embodiments, the method can include removing the first trocar and the second trocar after the disposing the solid tube. In some embodiments, the method can include coupling the ends of the bodily implant to body tissues.

In another general aspect, a method for the treatment of fecal incontinence can include making a bodily incision and inserting a first trocar and a second trocar through the bodily incision such that the first trocar and the second trocar collectively extend around a portion of an anal canal of a patient to form a continuous pathway around the anal canal. The method can include delivering a bodily implant through the continuous pathway.

In some embodiments, the making the bodily incision includes making a single perennial incision. In some embodiments, the making the bodily incision includes making a single incision at posteriolateral, anteriolateral and/or medial posterior locations of the anal canal. In some embodiments, the method can include engaging a distal end portion of the first trocar with a distal end portion of the second trocar. In some embodiments, the method can include disposing a hollow tubular sheath over the first trocar and the second trocar.

In some embodiments, the method can include removing the first trocar and the second trocar after the disposing the hollow tubular sheath. In some embodiments, the method can include disposing a hollow tubular sheath within a lumen defined by the first trocar and the second trocar. In some embodiments, the method can include removing the first trocar and the second trocar after the disposing the hollow tubular sheath. In some embodiments, the method can include disposing a solid tube in the hollow lumen of the first trocar and the second trocar. In some embodiments, the method can include removing the first trocar and the second trocar after the disposing the solid tube.

In yet another general aspect a method for the treatment of fecal incontinence can include making a first bodily incision at a first location and a second bodily incision at a second location different than the first location, wherein the first location and the second location are substantially anterior to an anal canal of a patient, and making a third bodily incision at a third location and a fourth bodily incision at a fourth location different than the third location, wherein the third location and the fourth location are substantially posterior to the anal canal. The method can include creating a first pathway around a first portion of the anal canal by inserting a first trocar into the first bodily incision and a second trocar into the second bodily incision such that the first trocar and the second trocar collectively extend around the first portion of the anal canal, and creating a second pathway around a second portion of the anal canal by inserting a third trocar into the third bodily incision and a fourth trocar into the fourth bodily incision such that the third trocar and the fourth trocar collectively extend around the second portion of the anal canal. The method can also include delivering a first bodily implant through the first pathway and a second bodily implant through the second pathway.

In some embodiments, the method can include engaging a distal end portion of the first trocar with a distal end portion of the second trocar. In some embodiments, the method can include engaging a distal end portion of the first trocar with a distal end portion of the second trocar. In some embodiments, the method can include engaging a distal end portion of the third trocar with a distal end portion of the fourth trocar. In some embodiments, the method can include disposing a hollow tubular sheath over the first trocar and the second trocar. In some embodiments, the method can include removing the first trocar and the second trocar after the disposing the hollow tubular sheath.

In some embodiments, the method can include disposing a hollow tubular sheath within a lumen defined by the first trocar and the second trocar. In some embodiments, the method can include removing the first trocar and the second trocar after the disposing the hollow tubular sheath. In some embodiments, the method can include disposing a solid tube in the hollow lumen of the first trocar and the second trocar. In some embodiments, the method can include removing the first trocar and the second trocar after the disposing the solid tube. In some embodiments, the method can include disposing a hollow tubular sheath over the third trocar and the fourth trocar.

In some embodiments, the method can include removing the third trocar and the fourth trocar after the disposing the hollow tubular sheath. In some embodiments, the method can include disposing a hollow tubular sheath within a lumen defined by the third trocar and the fourth trocar. In some embodiments, the method can include removing the third trocar and the fourth trocar after the disposing the hollow tubular sheath. In some embodiments, the method can include disposing a solid tube in the hollow lumen of the third trocar and the fourth trocar. In some embodiments, the method can include removing the third trocar and the fourth trocar after the disposing the solid tube. In some embodiments, the first portion of the anal canal is disposed apart from the second portion of the anal canal.

In yet another general aspect, a method for the treatment of fecal incontinence can include making a first bodily incision at a first location substantially anterior to an anal canal of a patient, and making a second bodily incision at a second location substantially posterior to the anal canal of the patient. The method can include inserting a first trocar and a second trocar through the first bodily incision such that the first trocar and the second trocar collectively extend about a first portion of the anal canal to form a first continuous pathway around the anal canal and inserting a third trocar and a fourth trocar through the second bodily incision such the third trocar and the fourth trocar collectively extend about a second portion of the anal canal to form a second continuous pathway around the anal canal. The method can also include delivering a first bodily implant through the first continuous pathway formed around the anal canal, and delivering a second bodily implant through the second continuous pathway formed around the anal canal. In some embodiments, the first portion of the anal canal is disposed apart from the second portion of the anal canal.

In yet another general aspect, a device for treatment of fecal incontinence can include a first member having two end portions and a middle portion disposed between the two end portions where the middle portion of the first member can be configured to surround a first side of an anal canal of a patient. The device can include a second member having two end portions and a middle portion disposed between the two end portions where the middle portion of the second member can be configured to surround a second side of the anal canal. The second side can be substantially opposite to the first side and the second member can be configured to be longitudinally spaced from the first member.

In some embodiments, the first member is a first bodily implant and the second member is a second bodily implant. In some embodiments, the first member and the second member form a noose structure upon placement within the patient's body. In some embodiments, at least one of the first member and the second member includes a strip extending along a length between a first end portion of the strip and a second end portion of the strip where the strip can have a set of first projections and a set of second projections extending along at least a portion of a longitudinal edge of the strip. The set of the first projections can be inclined toward the second end portion of the strip and the set of the second projections inclined toward the first end portion of the strip.

The present invention has been disclosed and described in terms of the treatment of human fecal incontinence. It must be appreciated by a person ordinarily skilled in the art that the present invention may find applications in the treatment of several other problems such as urinary incontinence, vaginal prolapse, anal prolapse, breast surgery, and the like.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A method for the treatment of fecal incontinence, the method comprising:
   disposing a bodily implant proximate to an anal canal of a patient, the bodily implant having a strip extending along a length between a first end portion and a second end portion, the strip having a set of first projections along one or more edges of the first end portion and a set of second projections along one or more edges of the second end portion, the strip having a projectionless portion between the set of the first projections and the set of the second projections, the set of the first projections inclined toward the second end portion of the strip and the set of the second projections inclined toward the first end portion of the strip;
   securing the set of first projections to a first portion of body tissue, the set of the first projections allowing movement of the bodily implant with respect to the first portion of the body tissue in a first direction and restricting movement of the bodily implant with respect to the first portion of the body tissue in a second direction;
   securing the set of the second projections to a second portion of the body tissue, the set of the second projections allowing movement of the bodily implant with respect to the second portion of the body tissue in the second direction and restricting movement of the bodily implant with respect to the second portion of the body tissue in the first direction, wherein the projectionless portion at least partially surrounds a portion of the body tissue proximate to the anal canal of the patient;
   inserting an elongate member across a pathway within a body of the patient using one or more insertion devices, wherein, during insertion, distal edges of the elongate member apply a push force on the bodily implant causing the first set of projections and/or the second set of projections to separate from the first portion of the body tissue and/or the second portion of the body tissue;
   adjusting a position of the bodily implant and
   removing the elongate member to re-engage the first set of projections and/or the second set of projections with the body tissue.

2. The method of claim 1 wherein the portion of the body proximate to the anal canal of the patient is a tear in bodily tissue, and the first portion of the body tissue is disposed on a first side of the tear in bodily tissue and the second portion of the body tissue is disposed on a second side of the tear in bodily tissue.

3. The method of claim 1 further comprising:
   pulling the first end of the strip to adjust the position of the bodily implant within the body of the patient.

4. The method of claim 1, wherein the elongate member is a hollow tubular sheath.

5. The method of claim 1, wherein the set of the first projections and the set of the second projections are formed with the same material as the strip.

6. The method of claim 1, wherein the set of the first projections and the set of the second projections are formed with a first biocompatible material and the strip is formed with a second biocompatible material different than the first biocompatible material.

7. The method of claim 1, wherein the set of the first projections includes a first biological material and the set of the second projections include a second biological material different than the first biological material.

8. The method of claim 1, wherein the strip includes multiple interwoven strands that collectively form an interlocked structure of an array of cells.

9. The method of claim 1, wherein the set of the first projections and the set of the second projections are integrally formed with the strip.

* * * * *